United States Patent
Enoki et al.

(10) Patent No.: US 9,238,797 B2
(45) Date of Patent: Jan. 19, 2016

(54) METHOD FOR PRODUCTION OF PLURIPOTENT STEM CELL

(75) Inventors: Tatsuji Enoki, Otsu (JP); Fumiko Iwamoto, Otsu (JP); Toshikazu Nishie, Otsu (JP); Takahiro Marui, Otsu (JP); Fuyuko Takashima, Otsu (JP); Ikunoshin Kato, Otsu (JP)

(73) Assignee: TAKARA BIO INC., Shiga (JP)

( * ) Notice: Subject to any disclaimer, the term of this patent is extended or adjusted under 35 U.S.C. 154(b) by 332 days.

(21) Appl. No.: 13/003,262

(22) PCT Filed: Jul. 7, 2009

(86) PCT No.: PCT/JP2009/062364
§ 371 (c)(1),
(2), (4) Date: Jan. 7, 2011

(87) PCT Pub. No.: WO2010/004989
PCT Pub. Date: Jan. 14, 2010

(65) Prior Publication Data
US 2011/0117653 A1    May 19, 2011

(30) Foreign Application Priority Data

Jul. 7, 2008  (JP) ................................ 2008-177155
Sep. 8, 2008  (JP) ................................ 2008-230040
Oct. 9, 2008  (JP) ................................ 2008-262861
Jan. 20, 2009  (JP) ................................ 2009-010214
Mar. 4, 2009  (JP) ................................ 2009-050694

(51) Int. Cl.
*C12N 5/074*    (2010.01)

(52) U.S. Cl.
CPC ........ *C12N 5/0696* (2013.01); *C12N 2501/405* (2013.01); *C12N 2501/602* (2013.01); *C12N 2501/603* (2013.01); *C12N 2501/604* (2013.01); *C12N 2501/605* (2013.01); *C12N 2501/608* (2013.01); *C12N 2501/727* (2013.01); *C12N 2510/00* (2013.01); *C12N 2533/52* (2013.01); *C12N 2740/15043* (2013.01); *C12N 2740/15071* (2013.01)

(58) Field of Classification Search
CPC ........... C12N 5/0696; C12N 2501/405; C12N 2501/602; C12N 2501/603; C12N 2501/604; C12N 2501/605; C12N 2501/608; C12N 2501/727; C12N 2501/00; C12N 2533/52; C12N 2740/15043; C12N 2740/15071
See application file for complete search history.

(56) References Cited

U.S. PATENT DOCUMENTS

| 6,147,276 | A | 11/2000 | Campbell et al. |
| 6,472,204 | B1 | 10/2002 | Asada et al. |
| 2004/0018617 | A1 | 1/2004 | Hwang et al. |
| 2004/0058447 | A1 | 3/2004 | Ueno et al. |
| 2005/0063958 | A1 | 3/2005 | Symonds et al. |
| 2007/0166291 | A1 | 7/2007 | Benati et al. |
| 2009/0029462 | A1* | 1/2009 | Beardsley et al. ............ 435/366 |
| 2009/0162936 | A1 | 6/2009 | Marui et al. |
| 2009/0191159 | A1 | 7/2009 | Sakurada et al. |

FOREIGN PATENT DOCUMENTS

| JP | 2004057198 A | 2/2004 |
| JP | 2007535965 T | 12/2007 |
| JP | 2008307007 A | 12/2008 |
| WO | 9707669 A1 | 3/1997 |
| WO | 9718318 A1 | 5/1997 |
| WO | 0001836 A1 | 1/2000 |
| WO | 2006134871 A1 | 12/2006 |
| WO | 2008124133 A1 | 10/2008 |

OTHER PUBLICATIONS

Carstanjen et al. (2001) Heparin inhibits retrovirus binding to fibronectin as well as retrovirus gene transfer on fibronectin fragments. Journal of Virology 75(13): 6218-6222.*
Hayman et al. (1979) Distribution of fetal bovine serum fibronectin and endogenous rat cell fibronectin in extracellular matrix. Journal of Cell Biology 83: 255-259.*
Minucci et al. (2006) Histone deacetylase inhibitors and the promise of epigenetic (and more) treatments for cancer. Nature Reviews Cancer 6: 38-51.*
White et al. (2001) Monocyte-fibronectin interactions, via alpha(5)beta(1) integrin, induce expression of CXC chemokine-dependent angiogenic activity. The Journal of Immunology 167: 5362-5366.*
Campbell K.H.S. et al., "Sheep cloned by nuclear transfer from a cultured cell line", Nature, 1996, vol. 380, pp. 64-66.
ES Cell Culture Products, "http://www.invitrogen.cojp/products/celtcufture/I0828001_shtml", Invitrogen, 2003, Japan.
Kim D. et al., "Generation of Human Induced Pluripotent Stem Cells by Direct Delivery of Reprogramming Proteins", Cell Stem Cell, 2009, vol. 4, pp. 472-476.
Masaki H. et al, "Heterogeneity of pluripotent marker gene expression in colonies generated in human iPS cell induction culture", Stem Cell Research, 2008, vol. 1, pp. 105-115.
Mikkelson T. et al., "Dissecting direct reprogramming through integrative genomic analysis", Nature, 2008, doi: 10.1038/nature07056, pp. 1-8.
Nakagawa M. et al., "Generation of induced pluripotent stem cells without Myc from mouse and human fibroblasts", Nature Biotechnology, 2008, vol. 26, No. 1, pp. 101-106.

(Continued)

*Primary Examiner* — Thaian N Ton
(74) *Attorney, Agent, or Firm* — Browdy and Neimark, PLLC

(57) ABSTRACT

The present invention relates to a method for production of a cell population containing a pluripotent stem cell, said method comprising a step of treating a somatic cell which has been contacted with nuclear reprogramming factors under nutrient-starved condition, and/or a step of treating the somatic cell with an agent capable of arresting cell cycle. The present invention allows induction and growth of pluripotent stem cells at high frequency, and it also allows production of pluripotent stem cells with high efficiency. The nuclear reprogramming factors to be used may be any selected from the group consisting of OCT4, SOX2, c-MYC, KLF4, NANOG and LIN28.

3 Claims, 3 Drawing Sheets

(56) References Cited

OTHER PUBLICATIONS

Takashi K. et al., "Induction of Pluripotent Stem Cells from Adult Human Fibroblasts by Defined Factors", Cell, 2007, vol. 131, No. 5, pp. 861-872.

Wilmut I. et al., "Viable offspring derived from fetal and adult mammalian cells", Nature, 1997, vol. 385, pp. 810-813.

Yu J. et al., "Induced, Pluripotent Stem Cell Lines, Derived from Human Somatic Cells", Science, 2007, vol. 318, No. 5858, pp. 1917-1920.

Office Action issued in corresponding Chinese Patent Application No. 200980135775.7, dated Feb. 25, 2013, with English Translation.

In-Hyun Park et al., Nature: International Weekly Journal of Science, vol. 451,Dec. 23, 2007, pp. 141-146.

Danwei Huangfu et al., Nature Biotechnolocy, vol. 26, No. 7, Jul. 1, 2008 pp. 795-797.

Kazutoshi Takahashi et al., Cell, vol. 131, No. 5, Nov. 30, 2007, pp. 861-872.

Alfonso Quintas-Cardama et al., Human Gene Therapy, vol. I8, No. 12, Dec. 1, 2007, pp. I253-1260.

Prashant Mali et al., Stem Cells, vol. 26, No. 8, May 29, 2008, pp. I998-2005.

Supplementary European Search Report issued in corresponding European application No. 09794433.4, dated Jan. 23, 2013.

Danwei Huangfu et al., Nature Biotechnology, vol. 26, No. 7, Jul. 1, 2008 pp. 795-797.

Alfonso Quintas-Cardarna et al., Human Gene Therapy, vol. I8, No. 12, Dec. 1, 2007, pp. I253-1260.

Supplementary European Search Report issued in corresponding European application No. 09794433, dated Jan. 13, 2013.

Office Action issued in corresponding Japanese Patent Application No. 2010-519780, dated Jan. 14, 2014, with English Translation.

Office Action issued in corresponding Japanese Patent Application No. 2010-519780, dated Jan. 14, 2013, with English Translation.

Decision on Rejection issued in corresponding Chinese Patent Application No. 200980135775.7, dated Jul. 11, 20135, 2013, with English Translation.

Notice of Reexamination issued in the corresponding Chinese Patent Application No. 200980135775.7 on Mar. 11, 2015, and English translation.

Takahashi K. et al., "Induction of Pluripotent Stem Cells from Mouse Embryonic and Adult Fibroblasts Cultures by Defined Factors", Cell, 126(4):663-676 (2006).

Hanenberg et al., Colocalization of retrovirus and target cells on specific fibronectin fragments increases genetic transduction of mammalian cells, Nature Medicine, 2(8):876-882 (1996).

Office Action issued in the corresponding Korean Patent Application No. 2011-7002284, on May 26, 2015, with English translation.

Office Action issued in corresponding Chinese Patent Application No. 200980135775.7, dated May 16, 2012, with English Translation.

\* cited by examiner

βIII-tublin-positive cell
(ectoderm)

α-smooth muscle
-actin-positive cell
(mesoderm)

SEQUENCE LISTING

```
<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Primer hSOX2-F to amplify the SOX2 gene.

<400> SEQUENCE: 1
cccggatccg cggccgcatg tacaacatga tggagacgga g        41

<210> SEQ ID NO 2
<211> LENGTH: 39
<212> TYPE: DNA
<213> ORGANISM: Artificial Sequence
<220> FEATURE:
<223> OTHER INFORMATION: Primer hSOX2-R to amplify the SOX2 gene.
```

-continued

<400> SEQUENCE: 2
cctctagagt cgactcacat gtgtgagagg ggcagtgtg                                    39

<210> SEQ ID NO 3
<211> LENGTH: 42
<212> TYPE: DNA
<213> ORGANISM: Artificial Sequence
<220> FEATURE:
<223> OTHER INFORMATION: Primer hKLF4-F to amplify the KLF4 gene.

<400> SEQUENCE: 3
cccggatccg cggccgcatg gctgtcagcg acgcgctgct cc                               42

<210> SEQ ID NO 4
<211> LENGTH: 41
<212> TYPE: DNA
<213> ORGANISM: Artificial Sequence
<220> FEATURE:
<223> OTHER INFORMATION: Primer hKLF4-R to amplify the KLF4 gene.

<400> SEQUENCE: 4
cctctagagt cgacttaaaa atgcctcttc atgtgtaagg c                                41

<210> SEQ ID NO 5
<211> LENGTH: 25
<212> TYPE: DNA
<213> ORGANISM: Artificial Sequence
<220> FEATURE:
<223> OTHER INFORMATION: Primer IRES-F-SalI to amplify the IRES
      sequence.

<400> SEQUENCE: 5
taagtcgacg cccctctccc tcccc                                                  25

<210> SEQ ID NO 6
<211> LENGTH: 39
<212> TYPE: DNA
<213> ORGANISM: Artificial Sequence
<220> FEATURE:
<223> OTHER INFORMATION: Primer IRES-R-NotI to amplify the IRES
      sequence.

<400> SEQUENCE: 6
atatgcggcc gctgtggcca tattatcatc gtgttttc                                    39

<210> SEQ ID NO 7
<211> LENGTH: 20
<212> TYPE: DNA
<213> ORGANISM: Artificial Sequence
<220> FEATURE:
<223> OTHER INFORMATION: Primer OCT4EndoqP-F1 to amplify the endogenous
      OCT4 gene.

<400> SEQUENCE: 7
ttcgcaagcc ctcatttcac                                                        20

<210> SEQ ID NO 8
<211> LENGTH: 20
<212> TYPE: DNA
<213> ORGANISM: Artificial Sequence
<220> FEATURE:
<223> OTHER INFORMATION: Primer OCT4EndoP-R1 to amplify the endogenous
      OCT4 gene.

<400> SEQUENCE: 8
ttggaagctt agccaggtcc                                                        20

```
<210> SEQ ID NO 9
<211> LENGTH: 20
<212> TYPE: DNA
<213> ORGANISM: Artificial Sequence
<220> FEATURE:
<223> OTHER INFORMATION: Primer SOX2EndoP-F2 to amplify the endogenous
      SOX2 gene.

<400> SEQUENCE: 9
aacagcatgg agaaaacccg                                                  20

<210> SEQ ID NO 10
<211> LENGTH: 20
<212> TYPE: DNA
<213> ORGANISM: Artificial Sequence
<220> FEATURE:
<223> OTHER INFORMATION: Primer SOX2EndoP-R2 to amplify the endogenous
      SOX2 gene.

<400> SEQUENCE: 10
gcaaacttcc tgcaaagctc                                                  20
```

METHOD FOR PRODUCTION OF PLURIPOTENT STEM CELL

TECHNICAL FIELD

The present invention relates to a method for production of a pluripotent stem cell having an ability to differentiate into a variety of cells.

BACKGROUND ART

A pluripotent stem cell, which is capable of differentiating into all cell lines of organism, has a potential ability to differentiate into an arbitrary cell type, and generate an arbitrary type of tissue or organ. Accordingly, application of the cell to new therapies of regenerating and supplementing a lost cell in an organism (regeneration medicine) is being expected. Furthermore, the cell has availabilities as a research tool in the field of embryology, molecular biology and pharmacy.

As a pluripotent stem cell, an embryonic stem cell (ES cell), which is a cell strain established from an inner cell mass among an early embryo at a stage called blastocyst, is known. However, a human ES cell prepared by destructing a human embryo is objected frequently from an ethical point of view, and its study is restricted in many cases.

In order to overcome problems of the ES cells, a pluripotent stem cell, which is a cell strain induced by artificially introducing genes into a somatic cell without using an embryo (induced pluripotent stem cell (iPS cell): e.g., Non-Patent Document 1), was developed. The cell is prepared by artificially introducing genes involved in acquisition and maintenance of totipotency of a cell into a somatic cell. Currently, study is actively progressed for procedures for preparing the cell or methods for utilizing the cell.

The Non-Patent Document 1 discloses a method of preparing a human iPS cell by introducing genes encoding four kinds of peptides of OCT3/4, SOX2, c-MYC and KLF4. In addition, other researchers reported that a human iPS cell was prepared by introduction of genes encoding another four kinds of polypeptides of OCT4, SOX2, NANOG and LIN28 (Non-Patent Document 2). However, not all the somatic cells into which these genes have been introduced are induced into iPS cells and, actually, only parts thereof (0.02% or less of the total cell number) is merely introduced into iPS cells. In order to improve this efficiency, addition of an agent inhibiting methylation of DNA to a medium has been attempted (Non-Patent Document 3). In addition, since c-MYC is an oncogene, and a risk of canceration of the gene-introduced cell is unavoidable when the cells are applied to medicine, attempt of inducing iPS cells without c-MYC has been carried out. In this case, however, an induction efficiency is further reduced (0.001% or less of the total cell number). Like this, it cannot be said yet that the technique of preparing iPS cells has been established under current circumstances.

PRIOR ART DOCUMENTS

Non-Patent Documents

Non-Patent Document 1: Cell, vol. 131, pp. 861-872, 2007
Non-Patent Document 2: Science, vol. 318, pp. 1917-1920, 2007
Non-Patent Document 3: Nature, doi:10. 1038/nature 07056, 2008

SUMMARY OF THE INVENTION

Problems to be Solved by the Invention

In order to try to utilize a pluripotent stem cell, it is urgently needed to develop a procedure of preparing the cell with efficiency. An object of the present invention is to improve induction efficiency of a pluripotent stem cell, and promote research and utilization of the cell.

Means to Solve the Problems

In order to solve the aforementioned problems, the present inventors intensively made an effort and, as a result, found out that, upon culturing a somatic cell which has been contacted with the factors involved in reprogramming of a nucleus (herein, also referred to as nuclear reprogramming factors), by treating the cell under the nutrient-starved conditions, an ES cell-like cell, that is, a stem cell retaining pluripotency is induced at a high frequency, and a pluripotent stem cell can be produced with high efficiency and stably, resulting in completion of the present invention. In addition, it was found out that, when a retrovirus vector(s) carrying genes encoding the nuclear reprogramming factors is introduced into a somatic cell in the presence of a functional substance having the activity of binding to retrovirus, an efficiency of inducing a pluripotent stem cell is improved, and a pluripotent stem cell can be obtained with higher frequency, as compared with the conventional method using polybrene, resulting in completion of the present invention.

That is, to outline the present invention, the first invention of the present inventions relates to a method for production of a cell population containing a pluripotent stem cell, and is characterized by comprising a step of treating a somatic cell which has been contacted with nuclear reprogramming factors under the nutrient-starved condition, and/or a step of treating the somatic cell with an agent capable of arresting cell cycle. As a aspect of the first invention, the method for production wherein the step of treatment under the nutrient-starved condition is a step of treatment under the protein-starved condition is provided, and a method for production, wherein the step of treatment under the protein-starved condition is a step of culturing a somatic cell which has been contacted with the nuclear reprogramming factors, using a medium having a low protein concentration, for example, a medium having protein concentration of 0 to 0.5%, is provided. In addition, a method for production, wherein the somatic cell which has been contacted with the nuclear reprogramming factors is a somatic cell selected from the group consisting of a somatic cell which has been cultured in a culture medium into which the nuclear reprogramming factors have been added, a somatic cell into which the nuclear reprogramming factors have been introduced, a somatic cell into which genes encoding the nuclear reprogramming factors have been introduced, and a somatic cell in which expressions of the nuclear reprogramming factor are induced with an agent, is provided. Further, a method for production, wherein the nuclear reprogramming factors are selected from the group consisting of OCT4, SOX2, c-MYC, KLF4, NANOG and LIN28, is provided.

The second invention of the present invention relates to a method for production of a cell population containing a pluripotent stem cell, comprising the following steps:
(1) a step of contacting nuclear reprogramming factors with a somatic cell, and (2) a step of treating the somatic cell obtained in (1) under the nutrient-starved condition, and/or treating the somatic cell with an agent capable of arresting cell cycle.

As a aspect of the second invention, the method for production, wherein the step (1) is carried out by an operation selected from the group consisting of addition of nuclear reprogramming factors to a culturing medium, introduction of the nuclear reprogramming factors or genes encoding the factors into a somatic cell, and induction of expression of the factors in the somatic cell with an agent, is provided. In addition, the method for production, wherein the step of treatment under the nutrient-starved condition of the step (2) is a step of treatment under the protein-starved condition, is provided, and the method for production, wherein the step of treatment under the protein-starved condition is carried out by culturing the cell using a medium having a low protein concentration, for example, a medium having protein concentration of 0 to 0.5% (w/v) is provided. Additionally, the method for production, wherein a cell death suppressing agent is contained in the medium used in the step of treatment under the protein-starved condition, is also provided. Further, the method for production, wherein the nuclear reprogramming factors are selected from the group consisting of OCT4, SOX2, c-MYC, KLF4, NANOG and LIN28, is also provided.

The third invention of the present invention provides a method for production of a pluripotent stem cell, said method comprising a step of producing a cell population containing a pluripotent stem cell via the first and second invention, and a step of isolating a pluripotent stem cell from the resulting cell population.

The fourth invention of the present invention relates to a method for production of a cell population containing a pluripotent stem cell, said method comprising a step of infecting a somatic cell with a retrovirus vector(s) carrying genes encoding the nuclear reprogramming factors in the presence of a functional substance having the activity of binding to a retrovirus. As a aspect of the fourth invention, the method for production, wherein the functional substance having the activity of binding to a retrovirus is a functional substance selected from the group consisting of fibronectin, fibroblast growth factor, type V collagen, a fragment of the polypeptide, polylysine, DEAE-dextran, and a functional substance having a retrovirus-binding site derived from the substance, is provided. In addition, the method for production, wherein the functional substance having the activity of binding to a retrovirus is a polypeptide having a heparin-II binding region of fibronectin, is also provided. Further, the method for production, wherein the genes encoding the nuclear reprogramming factors are genes encoding the nuclear reprogramming factors selected from the group consisting of OCT4, SOX2, c-MYC, KLF4, NANOG and LIN28, is also provided.

The fifth invention of the present invention provides a method for production of a pluripotent stem cell, said method comprising a step of producing a cell population containing a pluripotent stem cell via the fourth invention, and a step of isolating a pluripotent stem cell from the resulting cell population.

Effects of the Invention

Since the pluripotent stem cell obtained according to the present invention has a ability to differentiate into desired cells, and differentiated cells obtained by differentiating the pluripotent stem cell exhibits a high engraftment ability in a living body, the method of the present invention is extremely useful in basic research, and research for application to medicine.

MODE FOR CARRYING OUT THE INVENTION

Figure 1:
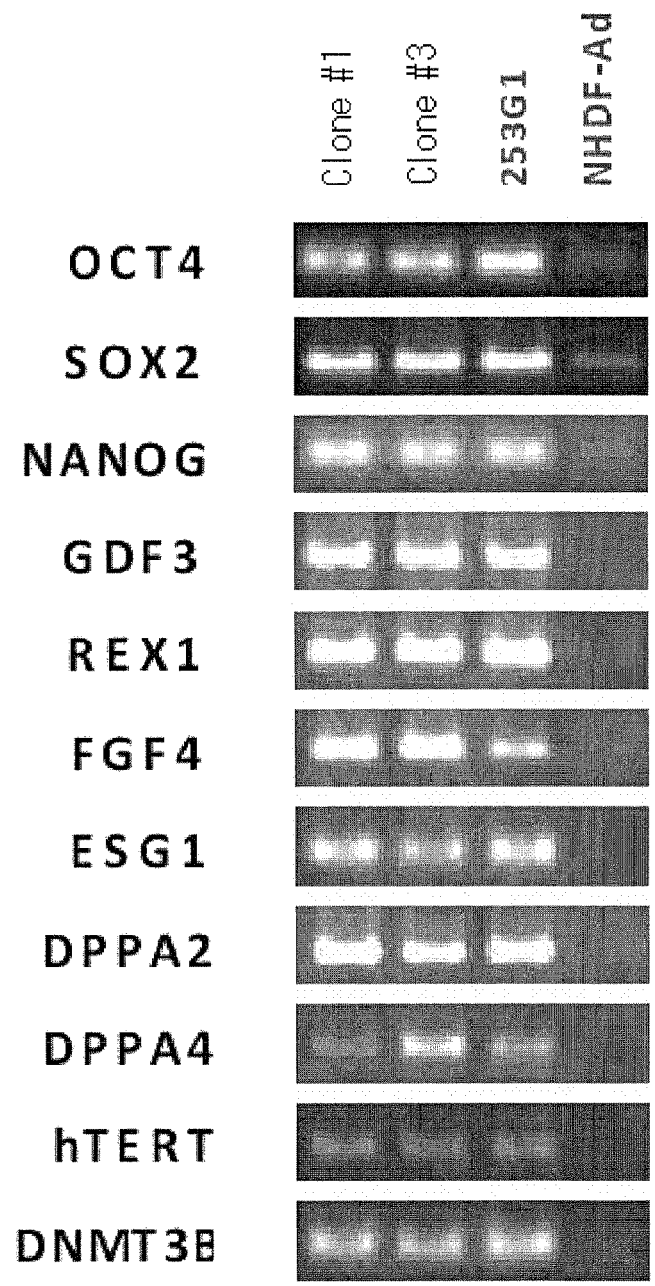
FIG. 1 is an electrophoretic photograph showing marker gene expression patterns of ES cells from clone #1 and clone #3, which are iPS cell clones established by the present invention, as well as 253G1 as a positive control, and a human adult skin fibroblast (NHDF-Ad) as a negative control.

The present invention is described in detail below.

In the method of the present invention, the somatic cell is referred to as a cell other than reproductive cell among cells constituting an organism. By contacting these somatic cells with nuclear reprogramming factors, reprogramming occurs, and the cells can obtain totipotency.

The step of contacting a somatic cell with nuclear reprogramming factors can be carried out by a method of adding polypeptides of the factors to a culture medium in contact with a somatic cell (e.g. Cell Stem Cell, vol. 4, pp. 472-476, 2009), a method of introducing polypeptides of the factors into a somatic cell, a method of introducing genes encoding the factors into a somatic cell, or a method of inducing expressions of the endogenous factors in a somatic cell with an agent such as a chemical substance etc. (e.g., 5-aza-2' deoxycytidine, BIX-01294, PD0325901, suberoylanilide hydroxamic acid, valproic acid etc.), or a combination of any of the aforementioned methods.

As the method of introducing genes encoding the nuclear reprogramming factors into a somatic cell, for example, a method of introducing a vector(s) into which genes encoding the nuclear reprogramming factors are incorporated into a somatic cell is included. The vector is not particularly limited, but an appropriate vector(s) selected from the known vectors can be used. For example, any of a method of using a virus vector(s), or a method of using a non-virus vector(s) can be used in the present invention. The details of these vectors have already been published in many documents, and a vector(s) may be used by appropriate selection from these many documents.

The virus vector as used above is not particularly limited, but usually, the known virus vector which is used in methods of gene transfer, for example, a retrovirus vector (including a lentivirus vector, and a pseudo-type vector), an adenovirus vector, an adeno-associated virus vector, a simianvirus vector, a vacciniavirus vector or a sendaivirus vector can be used. Particularly preferably, a retrovirus vector, a lentivirus vector or an adenovirus vector can be used. As the virus vector, a virus vector in which the replicating ability is deficient so that it cannot self-replicate in an infected cell is preferable. Alternatively, upon gene transfer, a substance which improves a gene transfer efficiency may be used. Examples of the substance which improves a gene transfer efficiency include a substance having the activity of binding to a virus vector, for example, a substance such as fibronectin and a fibronectin fragment. Preferably, a fibronectin fragment having a heparin binding site, for example, a fragment commercially available as Retronectin (registered trademark, CH-296, manufactured by TAKARA BIO INC.) can be used. The aforementioned substance is preferable in introducing a gene(s) using, particularly, a retrovirus vector or a lentivirus vector, without particularly limiting the present invention. Genes encoding the nuclear reprogramming factors can be used by incorporating them into one kind or a plurality of kinds of virus vectors. When two or more kinds of retrovirus vectors or lentivirus vectors are used, particularly, when virus infection is carried out plural times, it is preferable to use the substance which improves a gene transfer efficiency, particularly, fibronectin or the fibronectin fragment.

Conventionally, in gene transfer with a retrovirus vector for the purpose of inducing a pluripotent stem cell, polybrene which is a synthetic polycation having an activity of improving an efficiency of infecting a cell with retrovirus has been used. The present inventors first found out that, when genes encoding nuclear reprogramming factors are introduced into a somatic cell using a retrovirus vector in the presence of a functional substance having the activity of binding to the retrovirus without using polybrene, an efficiency of inducing a pluripotent stem cell is improved as compared with the case of using polybrene and, as a result, a pluripotent stem cell can be obtained with high frequency. That is, as another aspect of the present invention, a method for production of a cell population containing a pluripotent stem cell, comprising a step of infecting a somatic cell with a retrovirus vector(s) carrying genes encoding the nuclear reprogramming factors in the presence of a functional substance having the activity of binding to retrovirus is provided.

As described above, in the present aspect, a retrovirus vector including a lentivirus vector or a pseudo-type vector can be used.

In addition, as the functional substance having the activity of binding to retrovirus, there is not any particularly limitation as far as the substance is a substance having the activity, but for example, fibronectin, fibroblast growth factor, type V collagen, a fragment of the polypeptide, polylysine or DEAE-dextran can be used. Further, a functional substance having a retrovirus-binding site derived from the substance can be used. As the fragment of fibronectin, a fragment having a heparin-II binding region in a molecule is preferable, and such the fragment is described, for example, in International Publication No. 97/18318 pamphlet. As the fragment of fibronectin having a heparin-II binding region, Retronectin (registered trademark, CH-296, manufactured by TAKARA BID INC.) can be used. Alternatively, a substance which is functionally equivalent to these functional substances, for example, a functional substance having a heparin binding site can be also used. In addition, a mixture of the functional substances, a polypeptide containing the functional substance, a polymer of the functional substance, or a derivative of the functional substance can be used.

Further, a functional substance having the activity of binding to retrovirus and, at the same time, the activity of binding to a target cell, that is, the somatic cell into which a gene is tried to be introduced may be used together, or a functional substance having the activity of binding to retrovirus and a functional substance having the target cell binding activity may be used together. The functional substance having the target cell binding activity is not particularly limited, but the examples thereof include a substance having a ligand which binds to a target cell. Examples of the ligand include cell-adhering protein (fibronectin, laminin, collagen etc.) or a fragment thereof, hormone, cytokine, an antibody to an antigen on a cell surface, polysaccharides, glycoprotein, glycolipid, a sugar chain derived from a glycoprotein or a glycolipid, or a metabolite of a target cell.

In a preferable aspect of the present invention, the functional substance is used in the state where it is immobilized on, for example, a container (a plate, a petri dish, a flask or a bag) or a carrier (microbeads etc.) used in cell culturing.

According to the method of the present invention, since a pluripotent stem cell can be obtained at a higher efficiency than the conventional method even using a low concentration of virus, it is possible to considerably reduce an amount of virus used.

In addition, as shown in the following Examples, according to the present invention, even when only three kinds of genes encoding OCT4, SOX2 and KLF4 are introduced into a somatic cell, a pluripotent stem cell can be obtained at a higher efficiency than the conventional method.

The non-virus vector as used above is not particularly limited, but the examples thereof include a plasmid vector, and this can be introduced by a method of introduction using a carrier such as liposome, or ligand-polylysine, a calcium phosphate method, an electroporation method, or a particle gun method.

The genes encoding the nuclear reprogramming factors can be usually used by inserting them into a virus vector(s) or a non-virus vector(s) so that they are expressed under control of an appropriate promoter(s). As the promoter, any of a promoter which promotes expression constitutively, a promoter whose expression is induced by an agent (e.g., tetracycline or doxorubicin), etc. can be used. In addition, in order to attain efficient transcription of the genes, other regulation elements which cooperate with the promoter or a transcription initiating site, for example, an enhancer sequence or a terminator sequence may be present in the vector. In addition, only a gene encoding one kind of a factor among the nuclear reprogramming factors may be incorporated into one vector, and genes encoding a plurality of factors may be used by incorporating into one vector. Further, in addition to genes encoding the factors, a gene which can be a marker for confirming introduction of the genes (e.g., a drug resistance gene, a gene encoding a reporter enzyme, or a gene encoding a fluorescent protein) may be incorporated.

As the nuclear reprogramming factors used in the present invention, OCT4, SOX2, c-MYC, KLF4, NANOG, or LIN28 is known, and usually, a plurality of them, preferably, two to three kinds or more are contacted with a somatic cell. Information of the amino acid sequences of factors derived from various organisms (e.g., human, mouse), and information of the nucleotide sequences of genes encoding the factors are available from database. The genes encoding the factors can be isolated, or artificially synthesized, and obtained based on sequence information available from the database. Further, the factors (polypeptide) can be also obtained from a culture obtained by culturing transformants into which these genes have been introduced.

A method of preparing a pluripotent stem cell using genes encoding the nuclear reprogramming factors is described below.

(1) Step of Contacting Nuclear Reprogramming Factors with a Somatic Cell

The somatic cell used in the present invention is not particularly limited, thus, an arbitrary somatic cell can be used. For example, somatic cells such as fibroblast, precursor fat cell, liver cell, hemocyte, skin keratinocyte, mesenchymal stem cell, hematopoietic stem cell, or neural stem cell can be used. The somatic cell may be any of a somatic cell collected from a living body, or a somatic cell established as a cell strain. When it is desired that a prepared pluripotent stem cell or a cell differentiated from the cell is transplanted into a living body, it is preferable to induce a pluripotent stem cell from a somatic cell collected from the living body itself.

The genes encoding the nuclear reprogramming factors are introduced into a somatic cell using the known vector(s) as described above, and the factors are expressed from the introduced gene. Thus, contact between the nuclear reprogramming factors and the somatic cell is carried out.

When gene transfer is carried out using a plurality of vectors into which genes encoding the nuclear reprogramming factors are incorporated, respective vectors may be sequentially introduced into a somatic cell, or a mixture of vectors is prepared, and the vectors may be introduced into a somatic cell simultaneously.

(2) Step of Treating a Somatic Cell which has been Contacted with the Nuclear Reprogramming Factors, Under the Nutrient-Starved Condition.

By exposing the somatic cell which has been contacted with the nuclear reprogramming factors, for example, the somatic cell obtained in the step described in (1), to the nutrient-starved conditions, a frequency or a yield of induction and growth of pluripotent stem cells can be improved, and pluripotent stem cells can be produced with high efficiency. Herein, the exposure to the nutrient-starved conditions means that cells are cultured in a medium in which a specified component among components which are nutrient sources of the cells, for example, an amino acid, a protein, a carbohydrate, a lipid, an organic acid, or vitamins is not contained, or a concentration thereof is reduced (hereinafter, described as a nutrient-starved medium in some cases). Without particularly limiting the present invention, in the present invention, an operation of culturing cells in a medium in which a protein is not contained, or a concentration thereof is reduced, for example, a medium having protein concentration in a range of 0 to 0.5% (w/v) (hereinafter, described as a protein-starved medium in some cases), preferably, a medium in a range of 0 to 0.3% (w/v), further preferably a medium in a range of 0 to 0.1% (v/w) can be used. The protein concentration in the protein-starved medium can be measured via measurement of a standard protein (e.g., bovine serum albumin) by the known method, for example, the Lowry method, the Bradford method or a bicinchoninic acid (BCA) method.

A basal medium used in preparation of the protein-starved medium contains an energy source(s) such as an amino acid, saccharides or an organic acid, vitamins, a buffer component for adjusting a pH, or inorganic salts and, for example, the known medium such as DMEM or its modified medium, or other commercially available media can be also used. Components for maintaining pluripotency which are usually added to a medium for ES cells or iPS cells, for example, a growth factor such as leukemia inhibitory factor (LIF), basic fibroblast growth factor (bFGF), transforming growth factor-β1 (TGF-β1), or ciliary neurotrophic factor (CNTF), or other cytokines may be added. Further, serum or plasma may be added. In addition, the aforementioned various components are added to a medium so that the final total amount of proteins in a medium is in a range of 0 to 0.5% (w/v), preferably in a range of 0 to 0.3% (w/v), further preferably, in a range of 0 to 0.1% (w/v).

When the nutrient-starved medium which does not contain a specified component among components other than protein, or has the reduced concentration thereof is used, a medium is prepared so as not to contain the component, or by reducing a concentration thereof than a normal medium, additionally, or according to the known medium preparing method, as in the case of the protein-starved medium, and this medium may be subjected to culturing of a somatic cell which has been contacted with nuclear reprogramming factors. In addition, the component may be a single component, or a plurality of components. Alternatively, another component (other components) may be removed, or may be reduced in the protein-starved medium.

Treatment under the nutrient-starved condition can be carried out by continuing cultivation by exchanging a medium with the nutrient-starved medium, after subjecting the somatic cell which has been contacted with nuclear reprogramming factors, for example, the somatic cell obtained in the step described in (1) to coculture with a feeder cell. This medium exchange may be carried out by one time operation, or replacement of the medium with the nutrient-starved medium may be carried out by step-wisely reducing a concentration of a nutrient component. Thereafter, cultivation may be continued by exchanging the medium with a medium in which coculturing with a feeder cell is carried out. Alternatively, the somatic cell obtained in the step described in (1) as above is cultured using the nutrient-starved medium from initiation of cultivation and, thereafter, cultivation may be continued by exchanging the medium with a medium in which coculturing with a feeder cell is carried out. Treatment with the nutrient-starved medium is not limited to treatment which is carried out by the medium exchange, but the treatment may be other methods by which treatment is allowed under substantially the equivalent conditions. For example, the nutrient-starved state may be obtained by an operation such as a method of adding a protease to a medium to reduce protein concentration, or a method of adding lipase to reduce fat concentration, etc.

In addition, the feeder cell referred herein is not particularly limited as far as it can supply components effective for growth of induced pluripotent stem cells, but cells such as fibroblast (e.g., embryonic fibroblast), etc. are preferably used.

The number of somatic cells obtained in the step described in (1) to be seeded on feeder cells (herein, also referred to as seeded number) is not particularly limited as far as it is such the cell number that pluripotent stem cells are effectively induced, but usually, when a c-MYC gene is not introduced, about 9,000 cells/cm$^2$ are seeded. In the present invention, by decreasing the cell number of the somatic cells to be seeded, pluripotent stem cells can be further effectively induced. For example, the cell number is suitably 100 to 5000 cells/cm$^2$, preferably 250 to 5000 cells/cm$^2$.

Instead of the feeder cell, an extracellular matrix protein or a fragment thereof can be also used. It is preferable that the protein or a fragment thereof is used in the state where it is immobilized on an appropriate solid phase, for example, a container for culturing, etc.

That is, the method of production of a cell population containing a pluripotent stem cell of the present invention is characterized by comprising the step of treating a cell under the nutrient-starved condition in a whole period of culturing a somatic cell which has been contacted with the nuclear reprogramming factors, or in an arbitrary partial period thereof. Any methods comprising culturing a somatic cell, which has been contacted with nuclear reprogramming factors, under the nutrient-starved conditions are included in the present invention regardless the culturing period. In a preferable aspect of the present invention, the somatic cell is exposed to the nutrient-starved condition for at least 12 hours or longer, preferably 18 hours or longer in the period of step of culturing a somatic cell which has been contacted with the nuclear reprogramming factors. There is not particularly an upper limit of a time of the treatment, but from a view point of survival of cells, the somatic cell is treated for a period within 8 days, preferably within 6 days.

In addition, in the present invention, instead of the step of treatment under the nutrient-starved condition, a step of treating the somatic cell with an agent(s) capable of arresting cell cycle may be used. The agent capable of arresting cell cycle is not particularly limited, but cyclic-dependent kinase inhibitor such as butyrolactone I, olomoucine, roscovitine, Purvalanol A, Purvalanol B, DRB (5,6-dichlorobenzimidazole 1-β-D-ribofuranoside), SU9516, NU6102, NU6140, JNJ-7706621, CDK1/2 inhibitor II, flavopiridol, PD0332991, or CDK2 inhibitory peptide (TAT-LFG and TAT-LDL), an anti-cancer agent such as mitomycin, cisplatin, methotrexate, 5-fluorouracil, hydroxyurea, irinotecan hydrochloride, adriamycin, actinomycin D, etoposide, paclitaxel, or bleomycin, DHCP (4,5-dihydroxy-2-cyclopentene-1-one) or a derivative thereof, or rapamycin can be used. The amount of the agent capable of arresting cell cycle may be appropriately determined depending on the agent used.

Further, in the present invention, both of the step of treatment under the nutrient starved-condition, and the step of treatment with an agent(s) capable of arresting cell cycle may be carried out.

In addition, in a part of a culture period, a cell death suppressing agent may be used. The cell death suppressing agent is not particularly limited, but Y-27632 [(R)(+)-trans-4-(1-aminoethyl)-N-(4-pyridyl)cyclohexanecarboxyamide dihydrochloride], etc. can be used.

The condition for culturing the somatic cell which has been contacted with the nuclear programming factors is not particularly limited, whether it is the nutrient starved-condition, the condition for treatment with an agent capable of arresting cell cycle, or the normal condition, but the normal cell culturing condition can be used. For example, culturing at a humidity of 90 to 98%, a $CO_2$ concentration of 3 to 7%, and 30 to 40° C. can be used. Of course, exchange of a medium with a fresh medium at an appropriate time interval may be carried out.

A pluripotent stem cell obtained by the aforementioned method can be distinguished from other cells based on its morphological characteristic. Alternatively, the cell can be also confirmed by expression of a marker molecule which is an index of the undifferentiated state, such as alkaline phosphatase, stage-specific embryonic antigen (SSEA, e.g. SSEA-4, etc.), tumor rejection antigen (TRA)-1-60, TRA-1-81, OCT4 or NANOG. The expression of the molecule can be confirmed using, for example, an antibody recognizing the molecule. Regarding alkaline phosphatase, expression thereof can be confirmed based on its enzymatic activity.

Further, a pluripotent stem cell is isolated from a cell population obtained by the above methods, and a pluripotent stem cell separated from other cells can be obtained. Thus isolated pluripotent stem cell can be established as a cell strain by the known method. That is, a method for production of a pluripotent stem cell comprising steps of the method for production of a cell population containing a pluripotent stem cell of the present invention, and a step of isolating a pluripotent cell from the resulting cell population is provided in one aspect of the present invention.

Thus, according to the present invention, a pluripotent stem cell can be induced and grown at a higher frequency, as compared with the conventional method for production of a pluripotent stem cell (e.g., iPS cell), and production in which yield of the pluripotent stem cell is improved is allowed.

EXAMPLES

The present invention is described specifically below through Examples, but the present invention is not limited to the scopes of the following Examples at all.

Preparation Example 1

Cloning of Nuclear Reprogramming Factor Genes (1) Construction of pDON-AI-2-Neo-SOX2 and pDON-AI-2-Neo-KLF4 Plasmids From the sequence information of NCBI database Accession No. NM_03106.2, synthetic primers hSOX2-F and hSOX2-R for amplifying a SOX2 gene having a nucleotide sequence described in SEQ ID No.: 1 or 2 were synthesized, respectively. In addition, from sequence information of NCBI database Accession No. NM_004235.3, synthetic primers hKLF4-F and hKLF4-R for amplifying a KLF4 gene having a nucleotide sequence described in SEQ ID No.: 3 or 4 were synthesized, respectively.

PCR was carried out with each of a primer pair of hSOX2-F and hSOX2-R, and a primer pair of hKLF4-F and hKLF-R, and PrimeSTAR (registered trademark) MAX PreMix (manufactured by TAKARA BIO INC.), and employing a cDNA synthesized with HumanBrainPolyA+RNA (manufactured by Clonetech) as a template. After completion of the reaction, the reaction solution was subjected to 1.0% agarose gel electrophoresis, and an about 1 kbp DNA fragment regarding the SOX2 gene, and an about 1.5 kbp DNA fragment regarding the KLF4 gene were extracted and purified. Then, the resulting DNA fragments were digested with restriction enzymes NotI (manufactured by TAKARA BIO INC.) and SalI (manufactured by TAKARA BIO INC.) and purified to obtain a SOX2 fragment and a KLF4 fragment.

The SOX2 fragment and the KLF4 fragment were mixed with pDON-AI-2 Neo DNA (manufactured by TAKARA BIO INC.) which had been similarly digested with NotI-SalI, respectively, and ligated using DNA Ligation Kit <Mighty Mix> (manufactured by TAKARA BIO INC.). With this reaction product, *Escherichia coli* JM109 (manufactured by TAKARA BIO INC.) was transformed to obtain a transformant.

From plasmids prepared from the transformant, a plasmid in which an objective DNA fragment had been inserted was selected to obtain recombinant plasmids pDON-AI-2-Neo-SOX2 and pDON-AI-2-neo-KLF4. This pDON-AI-2-Neo-SOX2 is a plasmid comprising an open reading frame encoding the SOX2 polypeptide contained in NM_003106.2. And, pDON-AI-2-Neo-KLF4 is a plasmid comprising a sequence encoding the KLF4 polypeptide contained in NM_004235.3.

(2) Construction of pDON-AI-2-Neo-OCT4, pDON-AI-2-Neo-LIN28 and pDON-AI-2-Neo-NANOG Plasmids Based on the sequence information of NCBI database accession Nos. NM_002701.4, NM_024674.4, and NM_024865.2, artificial synthetic genes encoding respective polypeptides of OCT4, LIN28 and NANOG, respectively, were synthesized. The artificial synthetic genes have a three nucleotides sequence immediately before CDS and a recognition sequence of a restriction enzyme NotI at a 5'-end, and a recognition sequence of a restriction enzyme SalI at a 3' end, in addition to a nucleotide sequence of an open reading frame encoding each polypeptide. Three kinds of artificial synthetic genes were ligated with pDON-AI-2 Neo utilizing a recognition sequence of NotI and SalI, as in Preparation Example 1-(1), to obtain recombinant plasmids pDON-AI-2-

Neo-OCT4, pDON-AI-2-Neo-LIN28 and pDON-AI-2-Neo-NANOG in which each gene was inserted.

Preparation Example 2

Preparation of a Retrovirus Vector (1) Transfer into pDON-AI-2 and pDON-5 Plasmid Vectors PDON-AI-2-Neo-OCT4, pDON-AI-2-Neo-SOX2, pDON-AI-2-Neo-KLF4, pDON-AI-2-Neo-LIN28, and pDON-AI-2-Neo-NANOG prepared by Preparation Example 1 were treated with a restriction enzyme NotI and SalI, respectively, and fragments generated by subjecting to 1.0% agarose electrophoresis were separated on a gel. Fragments containing open reading frames encoding respective polypeptides were extracted and purified from a gel, each of the fragments was mixed with pDON-5 DNA (manufactured by TAKARA BIO INC.) which had been similarly digested with NotI-SalI, and ligated using DNA Ligation Kit <Mighty Mix> (manufactured by TAKARA BIO INC.). From thus made recombinant plasmids, plasmids in which each gene was correctly inserted were selected, and they were named pDON-5-OCT4, pDON-5-SOX2, pDON-5-KLF4, pDON-5-LIN28, and pDON-5-NANOG, respectively.

Regarding three genes of OCT4, KLF4 and LIN28, recombinant plasmids in which these were inserted into pDON-AI-2 DNA (manufactured by TAKARA BIO INC.), respectively, by the same operation were made, and they were named pDON-AI-2-OCT4, pDON-AI-2-KLF4, and pDON-AI-2-LIN28, respectively.

(2) Preparation of an IRES Fragment

Synthetic primers IRES-F-SalI and IRES-R-NotI for amplifying an IRES sequence, shown in SEQ ID Nos.:5 and 6 were synthesized. In order to amplify the IRES sequence, PCR was carried out by PrimeSTAR (registered trademark) DNA polymerase (manufactured by TAKARA BIO INC.) using pIRES2-ZsGreen 1 (manufactured by Clonetech) as a template DNA, and IRES-F-SalI and IRES-R-NotI as a primer. After completion of the reaction, the reaction solution was subjected to 0.1% agarose gel electrophoresis, and an about 0.6 kbp DNA fragment was extracted and purified. Then, this DNA fragment was digested with a restriction enzyme SalI and NotI, and purified to obtain an IRES fragment.

(3) Preparation of SOX2, LIN28, and NANOG Fragments pDON-5-SOX2, pDON-5-LIN28, and pDON-5-NANOG plasmids prepared in Preparation Example 2-(1) were treated with restriction enzymes NotI and HpaI, and fragments generated by subjecting to 1.0% agarose electrophoresis were separated on a gel. The fragment containing each gene of SOX2, LIN28, or NANOG (described as SOX2, LIN28, and NANOG fragments, respectively) was extracted and purified from a gel.

(4) Construction of pDON-AI-2-OCT4-IR-SOX2, pDON-AI-2-LIN28-IR-NANOG, pDON-5-OCT4-IR-SOX2, pDON-5-LIN28-IR-NANOG, and pDON-5-NANOG-IR-LIN28 Plasmids The fragments obtained by digesting pDON-AI-2-OCT4, pDON-AI-2-LIN28, pDON-5-OCT4, pDON-5-LIN28, and pDON-5-NANOG prepared in the Preparation Example 2-(1) with restriction enzymes SalI and HpaI, the IRES fragment prepared in (2) and SOX2, LIN28 and NANOG fragments prepared in (3) were mixed in a combination of Table 1, and ligated using DNA Ligation Kit <Mighty Mix> (manufactured by TAKARA BIO INC.).

TABLE 1

| Combinations of respective fragments for constructing plasmids | |
|---|---|
| pDON-AI-2-OCT4-IR-SOX2 | pDON-AI-2-OCT4, IRES Fragment, SOX2 Fragment |
| pDON-AI-2-LIN28-IR-NANOG | pDON-AI-2-LIN28, IRES Fragment, NANOG Fragment |
| pDON-5-OCT4-IR-SOX2 | pDON-5-OCT4, IRES Fragment, SOX2 Fragment |
| pDON-5-LIN28-IR-NANOG | pDON-5-LIN28, IRES Fragment, NANOG Fragment |
| pDON-5-NANOG-IR-LIN28 | pDON-5-NANOG, IRES Fragment, LIN28 Fragment |

From thus prepared recombinant plasmids, plasmids in which each gene is correctly inserted were selected, and named pDON AI-2-OCT4-IR-SOX2, pDON-AI-2-LIN28-IR-NANOG, pDON-5-OCT4-IR-SOX2, pDON-5-LIN28-IR-NANOG or pDON-5-NANOG-IR-LIN28. The pDON-AI-2-OCT4-IR-SOX2 is a plasmid in which an OCT4 gene, IRES, and a SOX2 gene are inserted into pDON-AI-2 in an order from its 5'-end side. The pDON-AI-2-LIN28-IR-NANOG is a plasmid in which a LIN28 gene, IRES and a NANOG gene are inserted into pDON-AI-2 in an order from its 5'-end side. The pDON-5-OCT4-IR-SOX2 is a plasmid in which an OCT4 gene, IRES and a SOX2 gene are inserted into pDON-5 in an order from its 5'-end side. The pDON-5-LIN28-IR-NANOG is a plasmid in which a LIN28 gene, IRES and a NANOG gene are inserted into pDON-5 in an order from its 5'-end side. The pDON-5-NANOG-IR-LIN28 is a plasmid in which a NANOG gene, IRES and a LIN28 gene are inserted into pDON-5 in an order from its 5'-end side.

(5) Production of a Retrovirus Vector

The G3T-hi cell (manufactured by TAKARA BIO INC.) was suspended in 10F-DMEM [D-MEM (manufactured by Sigma) containing 10% bovine fetal serum (manufactured by Invitrogen) and 1% penicillin/streptomycin (manufactured by NACALAI TESQUE, INC.), 4 mL of the suspension was seeded on a 6 cm collagen-coated dish (manufactured by IWAKI CO., LTD.), and incubated in a $CO_2$ incubator at 37° C. for 24 hours.

10 μL of TransIT (registered trademark)-293 (manufactured by TAKARA BIO INC.) was mixed into 500 μL of OPTI-MEM (manufactured by Invitrogen), the mixture was allowed to stand at room temperature for 5 minutes. 2 μg of the pGP plasmid (manufactured by TAKARA BIO INC.), 1 μg of the pE-Ampho plasmid (manufactured by TAKARA BIO INC.) and 2 μg of each recombinant plasmid prepared in Preparation Example 2-(1) and (4) were added, respectively, and these were mixed, and further allowed to stand at room temperature for 15 minutes. This mixed solution was added to the G3T-hi cell, culturing was continued and, after 24 hours, the medium was exchanged with 4 mL of 10F-DMEM. After culturing was further continued for 24 hours, a medium containing a virus was recovered, and filtered with a 0.45 μm filter to prepare a virus solution containing a retrovirus vector. And, 10F-DMEM was further added, culturing was continued and, after 24 hours, a medium containing a virus was recovered, and filtered with a 0.45 μm filter to prepare a virus solution, which was also used in an experiment. The virus solution was frozen and stored at −80° C. when it was not used immediately after preparation, and it was used by thawing upon use. Names of retrovirus vectors obtained from respective recombinant plasmids are shown in Table 2.

TABLE 2

List of retrovirus vectors

| Recombinant plasmid | Retrovirus vector |
|---|---|
| pDON-AI-2-OCT4-IR-SOX2 | DONAI2-am-OCT4-IR-SOX2 |
| pDON-AI-2-LIN28-IR-NANOG | DONAI2-am-LIN28-IR-NANOG |
| pDON-AI-2-KLF4 | DONAI2-am-KLF4 |
| pDON-5-OCT4-IR-SOX2 | DON5-am-OCT4-IR-SOX2 |
| pDON-5-LIN28-IR-NANOG | DON5-am-LIN28-IR-NANOG |
| pDON-5-NANOG-IR-LIN28 | DON5-am-NANOG-IR-LIN28 |
| pDON-5-KLF4 | DON5-am-KLF4 |
| pDON-5-LIN28 | DON5-am-LIN28 |
| pDON-5-NANOG | DON5-am-NANOG |

Preparation Example 3

Preparation of a Fluorescent Protein-Expressing Retrovirus Vector (1) Preparation of a Plasmid Vector The AcGFP1 gene was transferred from pAcGFP1 (manufactured by Clonetech) into pDON-AI-DNA (manufactured by TAKARA BIO INC.) to prepare pDON-AI-AcGFP1. Similarly, the mStrawberry gene was transferred from pmStrawberry Vector (manufactured by Clonetech) into pDON-AI-2 Neo DNA to prepare pDON-AI-2-Neo-mStrawberry.

(2) Production of a Retrovirus Vector

According to the same manner as that of Preparation Example 2-(5), a retrovirus vector DON-am-AcGFP1 was prepared from pDON-AI-AcGFP1, and a retrovirus vector DONAI2-am-mStrawberry was prepared from pDON-AI-2-Neo-mStrawberry.

Preparation Examples 4

Preparation of a Medium for a Mouse ES Cell (1) Preparation of 100×LIF

To 0.5 mL of the $10^6$ unit/mL leukemia inhibiting factor (LIF; ESGRO, manufactured by Invitorgen) were added 8.5 mL of Knockout DMEM (Dulbecco's modified eagle's medium, manufactured by Invitrogen) and 1.5 mL of Knockout Serum Replacement (manufactured by Invitrogen) to prepare 100×LIF.

(2) Preparation of a Medium for a Mouse ES Cell

A medium for a mouse ES cell was prepared by adding 75 ml of Knockout Serum Replacement (manufactured by Invitrogen), 5 mL of 100× Non-Essential Amino Acid mixture (NEAA mixture, manufactured by Lonza), 5 mL of 100 mM sodium pyruvate (manufactured by Lonza), 5 mL of 200 mM L-glutamine (manufactured by Lonza), 0.91 mL of 55 mM 2-mercaptoethanol (manufactured by Invitrogen), and 5 mL of 100×LIE prepared in (1) to 425 mL of Knockout DMEM.

Example 1

Induction of a Pluripotent Stem Cell (1) Immobilization of Retronectin on a Culture Plate Each 2 mL of a Retronectin (registered trademark, manufactured by TAKARA BIO INC.) solution diluted with an aqueous phosphate buffer solution (PBS) was added to each well of a non-treatment 6-well culture plate (manufactured by Becton, Dickinson and Company), to 20 to 25 µg/mL, and immobilization was carried out at 4° C. overnight or at room temperature for 2 hours. Thereafter, the solution was removed from each well, washed with PBS once, and stored at 4° C. until it was subjected to each experiment.

(2) Gene Transfer with a Retrovirus Vector, First Time

Each 700 µL of the virus solution prepared in Preparation Example 2 was added to each well of the Retronectin-immobilized culture plate prepared in (1) in a combination of Table 3, respectively, and this was centrifuged at 32° C. and 2,000×g for 2 hours.

TABLE 3

Combinations of retrovirus vectors

| Condition A | DONAI2-am-OCT4-IR-SOX2 |
| | DONAI2-am-LIN28-IR-NANOG |
| | DONAI2-am-KLF4 |
| Condition B | DON5-am-OCT4-IR-SOX2 |
| | DON5-am-NANOG-IR-LIN28 |
| | DON5-am-KLF4 |
| Condition C | DON5-am-OCT4-IR-SOX2 |
| | DON5-am-LIN28-IR-NANOG |
| | DON5-am-KLF4 |

Thereafter, the supernatant was removed from each well, washed with PBS once, and each 2 mL of human adult skin fibroblast (manufactured by Lonza) suspended in 10F-DMEM to $5 \times 10^4$ cells/mL was seeded on each well. After centrifugation at 32° C. and 500×g for 10 minutes, culturing was initiated in a $CO_2$ incubator at 37° C. (0 day of culture).

(3) Gene Transfer with a Retrovirus Vector, Second Time

Gene transfer for the second time was carried out on the first day of culture. Each 700 µL of virus solutions prepared by Preparation Example 2 were mixed in a combination of Table 3, and polybrene (hexadimethrine.bromide; manufactured by Aldrich) was added to a final concentration of 8 µg/mL to prepare a retrovirus vector mixed solution. The supernatant was removed from a culture plate which had been cultured in (2), and this retrovirus vector mixed solution was added. After culturing in a $CO_2$ incubator at 37° C. for 4 hours, 2 mL of 10F-DMEM was added. After further culturing for 2 days, the supernatant was removed, 2 mL of 10F-DMEM was added, and culturing was continued.

(4) Seeding on a Feeder Cell

An aqueous gelatin (manufactured by Sigma) solution having a final concentration of 1 mg/mL was added to a 10 cm petri dish (manufactured by IWAKI CO., LTD.), immobilized at room temperature for 1 hour or at 4° C. overnight, and washed to make a gelatin-immobilized petri dish. To this was seeded each $1 \times 10^6$ cells of SNL76/7 cell (manufactured by DS Pharma) treated with mitomycin C (manufactured by NACALAI TESQUE, INC.) having a final concentration of 12 µg/mL, and this was cultured in a $CO_2$ incubator at 37° C. overnight, thereby, a feeder cell was prepared.

The gene-introduced cell on the seventh day of culture made in (3) was recovered, and suspended in 10F-DMEM to $5 \times 10^4$ cells/mL. 10 mL of this suspension was seeded on the feeder cell, and culturing was continued.

(5) Protein Starvation or Methylation Inhibitor Treatment

On the eighth day of culture (after culturing for 1 day from seeding on the feeder cell), the supernatant was removed, and 10 mL of DMEM not containing serum (0F-DMEM: obtained by removing bovine fetal serum from 10F-DMEM) was added under Protein starvation treatment conditions. On the other hand, under the methylation inhibitor treatment conditions, 10 mL of a medium for ES cells [a medium for a primate ES cell (manufactured by ReproCELL Incorporated.) containing 1% penicillin/streptomycin, 4 ng/mL bFGF (manufactured by R&D systems)] was added, and 5-aza-2'-deoxycytidine (manufactured by Sigma) was further added to a final concentration of 1 μM. In addition, each treatment was carried out under conditions A, B and C described in Example 1-(2).

Two days after initiation of protein starvation treatment or methylation inhibition treatment (the tenth day from culturing initiation), the supernatant was removed, 10 mL of a medium for ES cells was added to each petri dish, and culturing was continued until the 28th day of culture. During this, the medium was exchanged at 1 to 2 days interval.

(6) Counting of Pluripotent Cell Colonies

The number of a pluripotent stem cell (iPS cell) under each condition of protein starvation of treatment or methylation inhibitor treatment under each of conditions A, B and C was counted on the 28th day of culture. The results thereof are shown in Table 4.

TABLE 4

Numbers of iPS cell colonies on the 28th day of culture

| Retrovirus combination condition | Cell treating method | Number of iPS cell colonies |
|---|---|---|
| Condition A | Protein starvation | 78 |
|  | Methylation inhibitor | 11 |
| Condition B | Protein starvation | 133 |
|  | Methylation inhibitor | 25 |
| Condition C | Protein starvation | 88 |
|  | Methylation inhibitor | 8 |

As shown in Table 4, in any combination of retrovirus vectors, the number of a pluripotent stem cell colony was considerably larger in the protein starvation-treated group than in the methylation inhibitor-treated group. That is, it was revealed that, by performing protein starvation treatment in a process of inducing a pluripotent stem cell, an efficiency of inducing a pluripotent stem cell is dramatically enhanced.

In addition, in the protein starvation-treated group, a pluripotent stem cell colony could be confirmed from the 16th day of culture under any condition, while in the methylation inhibitor-treated group, a pluripotent stem cell colony could be confirmed on the 26th day of culture. That is, was revealed that, by performing protein starvation treatment, a period for inducing a pluripotent stem cell can be considerably shortened.

(7) Measurement of Protein Concentration in the Medium

Regarding 10F-DMEM, DMEM and the medium for ES cells used in the above Example, a concentration of a protein contained in each of them was measured using the Bradford method (Coomassie Plus Protein Assay Reagent; manufactured by Pierce). As a result, it was confirmed that 5.5 mg/mL, 0.633 mg/mL and 24.1 mg/mL (all bovine serum albumin equivalent) protein was contained, respectively, in 10F-DMEM, DMEM and the medium for ES cells.

Example 2

Study of Protein-Starved Conditions (1) Immobilization of Retronectin on a Culture Plate Immobilization of Retronectin on a culture plate was carried out according to the same manner as that of Example 1-(1).

(2) Gene Transfer with a Retrovirus Vector, First Time

According to the same manner as that of Example 1-(2), gene transfer was carried out (0 day of culture), provided that centrifugation after cell seeding was not carried out. In addition, gene transfer was carried out in a combination of retrovirus vectors DON5-am-OCT4-IR-SOX2, DON5-am-LIN28-IR-NANOG and DONAI2-am-KLF4, respectively.

(3) Gene Transfer with a Retrovirus Vector, Second Time

Gene transfer for the second time was carried out on the first day of culture, according to the same manner as that of Example 2-(2).

(4) Seeding on a Feeder Cell

On the sixth day of culture, according to the same manner as that of Example 1-(4), the gene-introduced cell was seeded on a feeder cell, and culturing was continued, provided that a feeder cell (mitomycin C-treated SNL76/7 cell or STO cell (manufactured by Dainippon Pharma Co., Ltd.)) was seeded by each $1.5 \times 10^6$ cells. In addition, the gene-introduced cell was seeded by each $2.5 \times 10^5$ cells.

(5) Protein Starvation Treatment

On the seventh day of culture (after culturing for 1 day from seeding on a feeder cell), the supernatant was removed from a petri dish, and the cell was treated under the conditions shown in Table 5. In the Table, 0.5F-DMEM indicates DMEM containing 0.5% serum. After exchange with a medium for ES cells, culturing was continued under each condition until the 28th day of culture and, during this, the medium was exchanged at 1 to 2 days interval.

TABLE 5

Protein-starved conditions

| Condition | Treating method |
|---|---|
| Control | 10 mL of 10F-DMEM is added and, after culturing for 2 days, the medium is exchanged with a medium for ES cells. |
| Condition A | 10 mL of 0F-DMEM containing 10 μM Y27632 (manufactured by Calbiochem) and, after culturing for 2 days, the medium is exchanged with a medium for ES cells. |
| Condition B | 10 mL of 0F-DMEM containing 10 μM Y27632 is added and, after culturing for 3 days, the medium is exchanged with a medium for ES cells. |
| Condition C | 10 mL of 0F-DMEM containing 10 μM Y27632 is added and, after culturing for 4 days, the medium is exchanged with a medium for ES cells. |
| Condition D | 10 mL of 0F-DMEM containing 10 μM Y27632 is added and, after culturing for 5 days, the medium is exchanged with a medium for ES cells. |
| Condition E | 10 mL of 0.5F-DEME is added and, after culturing for 3 days, the medium is exchanged with a medium for ES cells. |

TABLE 5-continued

Protein-starved conditions

| Condition | Treating method |
|---|---|
| Condition F | 10 mL of 0.5F-DEME is added and, after culturing for 4 days, the medium is exchanged with a medium for ES cells. |
| Condition G | 10 mL of 0.5F-DEME is added and, after culturing for 5 days, the medium is exchanged with a medium for ES cells. |
| Condition H | 10 mL of 0F-DMEM is added and, after culturing for 4 days, the medium is exchanged with a medium for ES cells. |
| Condition I | 10 mL of 0F-DMEM is added and, after culturing for 5 days, the medium is exchanged with a medium for ES cells. |

(6) Counting of Pluripotent Stem Cells

The number of a pluripotent stem cell (iPS cell) colony under each condition was counted on the 28th day of culture. The results thereof are shown in Table 6.

TABLE 6

Numbers of iPS cell colonies on the 28th day of culture

| Condition | Number of an iPS cell colony |
|---|---|
| Control | 10 |
| Condition A | 54 |
| Condition B | 30 |
| Condition C | 78 |
| Condition D | 98 |
| Condition E | 33 |
| Condition F | 52 |
| Condition G | 98 |
| Condition H | 14 |
| Condition I | 64 |

As shown in Table 6, the number of a pluripotent stem cell colony was considerably larger in the protein starvation-treated group than in a control (non-treated). That is, it was revealed that, by performing protein starvation treatment in a process of inducing a pluripotent stem cell, an efficiency of inducing a pluripotent stem cell is dramatically enhanced. In addition, it was revealed that a pluripotent stem cell colony is stably obtained, by adding Y27632 [(R)(+)-trans-4-(1-aminoethyl)-N-(4-pyridyl)cyclohexanecarboxyamide dihydrochloride] which is one of substances inhibiting cell death during a protein starvation treatment term.

Example 3

Study of Cell Cycle Arresting Agent (1) Immobilization of Retronectin on a Culture Plate According to the same manner as that of Example 1-(1), immobilization of Retronectin on a culture plate was carried out.

(2) Gene Transfer with a Retrovirus Vector, First Time

According to the same manner as that of Example 1-(2), gene transfer was carried out (day 0 of culturing), provided that a plate was washed with PBS containing 1.5% human serum albumin, and centrifugation after cell seeding was not carried out. In addition, gene transfer was carried out in a combination of a retrovirus vector DON5-am-OCT4-IR-SOX2, DON5-am-LIN28-IR-NANOG, or DON5-am-KLF4.

(3) Gene Transfer with a Retrovirus Vector, Second Time

Gene transfer for the second time was carried out on the first day of culture, according to the same manner as that of Example 3-(2).

(4) Seeding on a Feeder Cell

On the seventh day of culture, according to the same manner as that of Example 1-(4), the gene-introduced cell was seeded on a feeder cell, and culturing was continued.

(5) Cell Cycle Arresting Agent Treatment

On the eighth day of culture (after culturing for 1 day from seeding on a feeder cell), the supernatant was removed from a petri dish, the medium was exchanged with a medium for ES cells, and a group to which Purvalanol A (manufactured by Sigma) was added so that a final concentration became 0.1 μM, 0.5 μM or 2 μM, and a group to which hydroxyurea (manufactured by Sigma) was added so that a final concentration became 10 μM or 100 μM were set. In addition, the agent was not added to a control. After culturing for 2 days, the medium was exchanged with a medium for ES cells, and culturing was continued until the 22nd day of culture. During this, the medium was exchanged at 1 to 2 days interval.

(6) Counting of a Pluripotent Stem Cell Colony

On the 22nd day of culture, the number of a pluripotent stem cell (iPS cell) colony under each condition was counted. The results thereof are shown in Table 7.

TABLE 7

Numbers of iPS cell colonies on the 22nd day of culture

| Condition | Number of iPS cell colonies |
|---|---|
| Control | 2 |
| Purvalanol A 0.1 μM | 28 |
| Purvalanol A 0.5 μM | 19 |
| Purvalanol A 2 μM | 19 |
| Hydroxyurea 10 μM | 26 |
| Hydroxyurea 100 μM | 13 |

As shown in Table 7, the number of a pluripotent stem cell colony was considerably larger in the Cell cycle arresting agent-treated group than in a control (non-treated). That is, it was revealed that, by performing treatment for arresting cell cycle in a process of inducing a pluripotent stem cell, an efficiency of inducing a pluripotent stem cell is dramatically enhanced.

Example 4

Study of the Seeding Number of the Gene-Introduced Cell (1) Immobilization of Retronectin on a Culture Plate According to the same manner as that of Example 1-(1), immobilization of Retronectin on a culture plate was carried out.

(2) Gene Transfer with a Retrovirus Vector, First Time

According to the same manner as that of Example 2-(2), gene transfer was carried out (day 0 of culturing). In addition, gene transfer was carried out in a combination of a retrovirus vector DON5-am-OCT4-IR-SOX2, DON5-am-LIN28-IR-NANOG, or DON5-am-KLF4.

(3) Gene Transfer with a Retrovirus Vector, Second Time

In gene transfer for the second time, on the first day of culture, each 700 μL of virus solutions were mixed in a combination of Example 4-(2), polybrene was added to a final concentration of 8 μg/mL to prepare a retrovirus vector mixed solution, the supernatant was removed from a plate on which the cell had been cultured, and this retrovirus vector mixed solution was added. After culturing for 1 day, the supernatant was removed, 2 mL of 10F-DMEM was added, and culturing was continued.

(4) Seeding on a Feeder Cell

On the sixth day of culture, according to the same manner as that of Example 2-(4), the gene-induced cell was seeded on a feeder cell, and culturing was continued, provided that a group of seeding each $0.62 \times 10^5$, $1.25 \times 10^5$, $2.5 \times 10^5$, or $5 \times 10^5$ cells of the gene-introduced cell was set.

(5) Protein Starvation Treatment

On the seventh day of culture (after culturing for 1 day from seeding on the feeder cell), the supernatant was removed from a petri dish, and 10 mL of 0F-DMEM was added. After culturing for 2 days, the supernatant was removed, 9 mL of a medium for ES cells was added to each petri dish, and culturing was continued until the 28th day of culture. During this, the medium was exchanged at 1 to 2 days interval.

(6) Counting of Pluripotent Stem Cell Colonies

On the 28th day of culture, the number of a pluripotent stem cell (iPS cell) colony under each condition was counted. In addition, an efficiency of inducing an iPS cell (%) was calculated as (iPS cell colony number÷gene-introduced cell seeding number)×100. The results thereof are shown in Table 8.

TABLE 8

Numbers of iPS cell colonies on the 28th day of culture

| Gene-introduced cell seeding number | Number of an iPS cell colony | iPS cell induction efficiency (%) |
|---|---|---|
| $0.62 \times 10^5$ | 80 | 0.129 |
| $1.25 \times 10^5$ | 131 | 0.105 |
| $2.5 \times 10^5$ | 155 | 0.062 |
| $5.0 \times 10^5$ | 23 | 0.0046 |

As shown in Table 8, as the seeding number of the gene-introduced cell was smaller, an efficiency of inducing a pluripotent stem cell colony was higher. That is, it was revealed that, by decreasing the seeding number of the gene-induced cell in a process of inducing a pluripotent stem cell, an efficiency of inducing a pluripotent stem cell is enhanced.

Example 5

Study of Protein-Starved Conditions-2

(1) Immobilization of Retronectin on a Culture Plate

According to the same manner as that of Example 1-(1), immobilization of Retronectin on a culture plate was carried out.

(2) Gene Transfer with a Retrovirus Vector, First Time

According to the same manner as that of Example 4-(2), gene transfer was carried out (day 0 of culturing).

(3) Gene Transfer with a Retrovirus Vector, Second Time

Gene transfer for the second time was carried out on the first day of culture, according to the same manner as that of Example 5-(2).

(4) Seeding on a Feeder Cell

On the sixth day of culture, according to the same manner as that of Example 2-(4), the gene-introduced cell was seeded on a feeder cell, and culturing was continued, provided that a 6-well culture plate (manufactured by Corning) was used as a culturing container, and a feeder cell was seeded by each $2.5 \times 10^5$ cells. In addition, the gene-introduced cell was seeded by each $2 \times 10^4$ cells.

(5) Protein Starvation Treatment

On the seventh day of culture (after culturing for 1 day from seeding on the feeder cell), the supernatant was removed from the 6-well culture plate, and the cell was treated under the conditions shown in Table 9. In addition, after exchange of the medium with a medium for ES cells, culturing was continued under each condition until the 28th day of culture and, during this, the medium was exchanged at 1 to 2 days interval.

TABLE 9

Protein-starved conditions

| Condition | Treating method |
|---|---|
| Control | Exchanged with a medium for ES cell. |
| Condition A | 2 mL of 10F-DMEM was added and, after culturing for 2 days, the medium was exchanged with a medium for ES cells. |
| Condition B | 2 mL of 10F-DMEM was added and, after culturing for 4 days, the medium was exchanged with a medium for ES cells. |
| Condition C | 2 mL of 10F-DMEM was added and, after culturing for 6 days, the medium was exchanged with a medium for ES cells. |
| Condition D | 2 mL of 0F-DMEM was added and, after culturing for 2 days, the medium was exchanged with a medium for ES cells. |
| Condition E | 2 mL of 0F-DMEM was added and, after culturing for 4 days, the medium was exchanged with a medium for ES cells. |

TABLE 9-continued

Protein-starved conditions

| Condition | Treating method |
| --- | --- |
| Condition F | 2 mL of 0F-DMEM was added and, after culturing for 6 days, the medium was exchanged with a medium for ES cells. |
| Condition G | 2 mL of 0F-DMEM containing 10 μM Y27632 was added and, after culturing for 2 days, the medium was exchanged with a medium for ES cells. |
| Condition H | 2 mL of 0F-DMEM containing 10 μM Y27632 was added and, after culturing for 4 days, the medium was exchanged with a medium for ES cells. |
| Condition I | 2 mL of 0F-DMEM containing 10 μM Y27632 was added and, after culturing for 6 days, the medium was exchanged with a medium for ES cells. |
| Condition J | 2 mL of 0.5F-DMEM was added and, after culturing for 2 days, the medium was exchanged with a medium for ES cells. |
| Condition K | 2 mL of 0.5F-DMEM was added and, after culturing for 4 days, the medium was exchanged with a medium for ES cells. |
| Condition L | 2 mL of 0.5F-DMEM was added and, after culturing for 6 days, the medium was exchanged with a medium for ES cells. |
| Condition M | 2 mL of 0.5F-DMEM containing 10 μM Y27632 was added and, after culturing for 2 days, the medium was exchanged with a medium for ES cells. |
| Condition N | 2 mL of 0.5F-DMEM containing 10 μM Y27632 was added and, after culturing for 4 days, the medium was exchanged with a medium for ES cells. |
| Condition O | 2 mL of 0.5F-DMEM containing 10 μM Y27632 was added and, after culturing for 6 days, the medium was exchanged with a medium for ES cells. |

(6) Counting of Pluripotent Stem Cell Colonies

On the 28th day of culture, the number of a pluripotent stem cell (iPS cell) colony under each condition was counted. The results thereof are shown in Table 10. The number in the Table indicates an average value of N=2.

TABLE 10

Numbers of iPS cell colonies on the 28th day of culture

| Condition | Number of an iPS cell colony |
| --- | --- |
| Control | 17.5 |
| Condition A | 21.0 |
| Condition B | 20.5 |
| Condition C | 32.5 |
| Condition D | 32.0 |
| Condition E | 28.0 |
| Condition F | 19.5 |
| Condition G | 29.0 |
| Condition H | 27.5 |
| Condition I | 26.5 |
| Condition J | 26.5 |
| Condition K | 33.5 |
| Condition L | 27.0 |
| Condition M | 28.0 |
| Condition N | 38.5 |
| Condition O | 37.5 |

As shown in Table 10, the number of a pluripotent stem cell colony was considerably larger in the protein starvation-treated group than in a control (non-treated). That is, it was revealed that, by performing protein starvation treatment in a process of inducing a pluripotent stem cell, an efficiency of inducing a pluripotent stem cell is dramatically enhanced. In addition, it was revealed that a pluripotent stem cell colony is obtained stably, by adding Y27632 [(R) (+)-trans-4-(1-aminoethyl)-N-(4-pyridyl)cyclohexanecarboxyamide dihydrochloride] which is one of substances inhibiting cell death during a protein-starvation treatment term.

Example 6

Study of the Seeding Number of the Gene-Induced Cell-2

(1) Immobilization of Retronectin on a Culture Plate

According to the same manner as that of Example 1-(1), immobilization of Retronectin on a culture plate was carried out.

(2) Gene Transfer with a Retrovirus Vector, First Time

According to the same manner as that of Example 4-(2), gene transfer was carried out (day 0 of culturing).

(3) Gene Transfer with a Retrovirus Vector, Second Time

Gene transfer for the second time was carried out on the first day of culture, according to the same manner as that of Example 6-(2).

(4) Seeding on a Feeder Cell

On the sixth day of culture, according to the same manner as that of Example 5-(4), the gene-introduced cell was seeded on a feeder cell, and culturing was continued, provided that a group of seeding the gene-introduced cell by each $2.5 \times 10^3$, $5 \times 10^3$, $1 \times 10^4$, $2 \times 10^4$, $4 \times 10^4$, or $8 \times 10^4$ cells was set.

(5) Protein Starvation Treatment

On the seventh day of culture (after culturing for 1 day from seeding on the feeder cell), the supernatant was removed from the 6-well culture plate, and 2 mL of 0F-DMEM or a medium for ES cells (control) was added. After culturing for 2 days, the supernatant was removed, 2 mL of a medium for ES cells was added to each well, and culturing was continued until the 28th day of culture. During this, the medium was exchanged at 1 to 2 days interval.

(6) Counting of Pluripotent Stem Cell Colonies

On the 28th day of culture, the number of a pluripotent stem cell (iPS cell) colony under each condition was counted. In addition, an iPS cell induction efficiency (%) was calculated as (iPS cell colony number÷gene-introduced cell seeding number)×100. The results thereof are shown in Table 11 and Table 12. Table 11 shows the results of the control group, and Table 12 shows the results of the protein starvation group.

TABLE 11

Numbers of iPS cell colonies on the 28th day of culture (control groups)

| Gene-introduced cell seeding number | Number of iPS cell colonies | iPS cell induction efficiency (%) |
|---|---|---|
| $2.5 \times 10^3$ | 8 | 0.32 |
| $5.0 \times 10^3$ | 9 | 0.18 |
| $1.0 \times 10^4$ | 8 | 0.08 |
| $2.0 \times 10^4$ | 18 | 0.09 |
| $4.0 \times 10^4$ | 2 | 0.005 |
| $8.0 \times 10^4$ | 3 | 0.00375 |

TABLE 12

Numbers of iPS cell colonies on the 28th day of culture (protein starvation groups)

| Gene-introduced cell seeding number | Number of iPS cell colonies | iPS cell induction efficiency (%) |
|---|---|---|
| $2.5 \times 10^3$ | 9 | 0.36 |
| $5.0 \times 10^3$ | 18 | 0.36 |
| $1.0 \times 10^4$ | 22 | 0.22 |
| $2.0 \times 10^4$ | 28 | 0.14 |
| $4.0 \times 10^4$ | 19 | 0.0475 |
| $8.0 \times 10^4$ | 3 | 0.00375 |

As shown in Tables 11 and 12, in the protein starvation-treated group than in a control (non-treated), and as the seeding number of the gene-introduced cell is smaller, an efficiency of inducing a pluripotent stem cell colony was higher. That is, it was revealed that, by performing protein starvation treatment to decrease the seeding number of the gene-introduced cell in a process of inducing a pluripotent stem cell, an efficiency of inducing a pluripotent stem cell is enhanced.

Example 7

Study of Method of Introducing a Gene

Regarding gene transfer with a retrovirus vector, introduction was carried out once or two times using Retronectin or polybrene, and induction of a pluripotent stem cell was carried out, followed by comparison. The set conditions are shown in Table 13.

TABLE 13

| Condition | Treating method |
|---|---|
| Condition A | Gene transfer with Retronectin once, without protein starvation treatment |
| Condition B | Gene transfer with Retronectin once, with protein starvation treatment |
| Condition C | Gene transfer with polybrene once, without protein starvation treatment |
| Condition D | Gene transfer with polybrene once, with protein starvation treatment |
| Condition E | Gene transfer with Retronectin two times, without protein starvation treatment |
| Condition F | Gene transfer with Retronectin two times, with protein starvation treatment |
| Condition G | Gene transfer with polybrene two times, without protein starvation treatment |
| Condition H | Gene transfer with polybrene two times, with protein starvation treatment |

(1) Immobilization of Retronectin on a Culture Plate

According to the same manner as that of Example 1-(1), immobilization of Retronectin on a culture plate was carried out.

(2) Gene Transfer with a Retrovirus Vector, First Time

Regarding gene transfer with Retronectin, according to the same manner as that of Example 4-(2), gene transfer was carried out. Gene transfer with polybrene was carried out as follows. That is, each 2 mL of human skin fibroblast suspended in 10F-DMEM to $5 \times 10^4$ cells/mL was seeded on each well of a 6-well culture plate one day before, and this was cultured for 1 day. Each 700 µL of the virus solutions prepared by Preparation Example 2 were mixed in a combination of the condition C of Table 3, polybrene was added to a final concentration of 8 µg/mL to prepare a retrovirus vector mixed solution, the supernatant was removed from the plate on which the cell had been cultured, this retrovirus vector mixed solution was added, and culturing was initiated (day 0 of culturing).

(3) Gene Transfer with a Retrovirus Vector, Second Time

Regarding groups in which second gene transfer is carried out, on the first day of culture, gene transfer with Retronectin was carried out according to the same manner as that of Example 4-(2). Gene transfer with polybrene was carried out according to the same manner as that of gene transfer with polybrene of Example 7-(2). That is, the supernatant was removed from the plate on which the cell had been cultured, a retrovirus vector mixed solution prepared similarly was added, and culturing was continued. After culturing for 1 day, the supernatant was removed, 2 mL of 10F-DMEM was added, and culturing was continued.

(4) Seeding on a Feeder Cell

On the sixth day of culture, according to the same manner as that of Example 5-(4), the gene-introduced cell was seeded on a feeder cell, and culturing was continued, provided that the gene-introduced cell was seeded by each $1.75 \times 10^4$ cells.

(5) Protein Starvation Treatment

On the seventh day of culture (after culturing for 1 day from seeding on the feeder cell), the supernatant was removed from the 6-well culture plate, and 2 mL of 0F-DMEM or a medium for ES cells (protein starvation treatment-free group) was added. After culturing for 2 days, the supernatant was removed, 2 mL of a medium for ES cells was added to each well, and culturing was continued until the 28th day of culture. During this, the medium was exchanged at 1 to 2 days interval.

(6) Counting of Pluripotent Stem Cell Colonies

On the 28th day of culture, the number of a pluripotent stem cell (iPS cell) colony under each condition was counted. The results thereof are shown in Table 14. The number in the Table indicates an average value of N=2.

TABLE 14

Numbers of iPS cell colonies on the 28th day of culture

| Condition | Number of iPS cell colonies |
|---|---|
| Condition A | 9.5 |
| Condition B | 25.5 |
| Condition C | 1.0 |
| Condition D | 7.0 |
| Condition E | 26.0 |
| Condition F | 30.0 |
| Condition G | 0.5 |
| Condition H | 1.0 |

As shown in Table 14, an efficiency of inducing a pluripotent stem cell was considerably higher by performing gene transfer with Retronectin than by performing gene transfer with polybrene. In addition, it was revealed that an induction efficiency is further enhanced by performing protein starvation treatment.

Example 8

Comparison of Methods of Introducing a Gene at Multiple Gene Transfer

At pluripotent stem cell induction, gene transfer is carried out using a plurality of retrovirus vectors in some cases. Then, as a method when gene transfer with a plurality of retrovirus vectors is carried out, gene transfer efficiencies by Retronectin and polybrene were compared.

(1) Immobilization of Retronectin on a Culture Plate

According to the same manner as that of Example 1-(1), immobilization of Retronectin on a culture plate was carried out, provided that a non-treatment 24-well culture plate (manufactured by Becton, Dickinson and Company) was used, and a Retronectin solution was added to each well by each 500 µL.

(2) Gene Transfer with a Retrovirus Vector

Gene transfer with Retronectin was carried out according to the same manner as that of Example 3-(2), provided that a retrovirus vector was a combination of DON-am-AcGFP1 and DONAI2-am-mStrawberry, and gene transfer was carried out by mixing each 250 µL of virus solutions. Further, a group of mixing 250 µL of a virus solution diluted 50-fold with 10F-DMEM was also set. In addition, a cell was suspended in a medium to $4 \times 10^4$ cells/mL, and each 500 µL was added to each well.

Gene transfer with polybrene was carried out in the same combination as that of retrovirus vectors according to the same manner as that of gene transfer with polybrene of Example 7-(2), provided that the cell was suspended in a medium to $4 \times 10^4$ cells/mL, and each 500 µL was added to each well of a 24-well culture plate (manufactured by Corning). In addition, virus solutions were mixed by each 250 µL, and polybrene was added to a final concentration of 4 µg/mL to prepare a retrovirus vector mixed solution. After culturing for 1 day, the supernatant was removed, 500 µL of 10F-DMEM was added, and culturing was continued.

(3) Measurement of a Gene Transfer Efficiency

After 3 days from gene transfer operation, the cells were recovered, and AcGFP1 positive and mStrawberry positive cells were measured with a flow cytometer (CytomicsFC500, manufactured by Beckmann Coulter Inc.). The results thereof are shown in Table 15. Table 15 shows a ratio of both positive cells in each gene transfer method.

TABLE 15

Ratio of double positive cells

| Gene transfer method | Ratio of double positive cells (%) |
|---|---|
| Gene transfer with Retronectin | 40.7 |
| Gene transfer with polybrene | 14.5 |
| Gene transfer with Retronectin, virus 50-fold dilution | 66.5 |
| Gene transfer with polybrene, virus 50-fold dilution | 18.6 |

As shown in Table 15, a ratio of cells in which both genes were introduced was considerably higher, as compared with gene transfer with polybrene, by performing gene transfer with Retronectin, when gene transfer was carried out using two kinds of retrovirus vectors. That is, since when a pluripotent stem cell is induced, two or more kinds of retrovirus vectors are used in many cases, it was thought that, by using Retronectin, a ratio of introduction of a plurality of genes becomes higher and, as a result, an efficiency of inducing a pluripotent stem cell is enhanced. In addition, it is thought that, by using a virus solution by dilution when gene transfer with Retronectin is carried out, a gene transfer efficiency is further enhanced and, as a result, it is possible to further enhance an efficiency of inducing a pluripotent stem cell.

Example 9

Comparison of Gene Transfer Methods at Multiple Genes Introduction-2

Gene transfer efficiencies using a plurality of retrovirus vectors with Retronectin or polybrene were further compared.

(1) Immobilization of Retronectin on a Culture Plate

According to the same manner as that of Example 8-(1), immobilization of Retronectin on a culture plate was carried out.

(2) Gene Transfer with a Retrovirus Vector

According to the same manner as that of Example 8-(2), gene transfer was carried out, provided that a group in which a virus solution is diluted 10-fold or 100-fold with 10F-DMEM was set.

(3) Measurement of a Gene Transfer Efficiency

According to the same manner as that of Example 8-(3), a gene transfer efficiency was measured, provided that measurement with a flow cytometer was carried out 5 days after gene transfer operation. The results thereof are shown in Table 16. Table 16 shows a ratio of both positive cells in each gene transfer method.

TABLE 16

Comparison of double positive cells

| Gene transfer method | Ratio of both positive cells |
|---|---|
| Gene transfer with Retronectin | 33.9 |
| Gene transfer with polybrene | 7.7 |
| Gene transfer with Retronectin, virus 10-fold dilution | 55.4 |
| Gene transfer with polybrene, virus 10-fold dilution | 36.0 |
| Gene transfer with Retronectin, virus 100-fold dilution | 67.6 |
| Gene transfer with polybrene, virus 100-fold dilution | 8.4 |

As shown in Table 16, a ratio of cells in which both genes were introduced was considerably higher, as compared with gene transfer with polybrene, by performing gene transfer in the presence of Retronectin, when gene transfer was carried out using two kinds of retrovirus vectors. That is, since when a pluripotent stem cell is induced, two or more retrovirus vectors are used in many cases, a ratio of introduction of a plurality of genes becomes higher by using Retronectin, and it was thought that, as a result, an efficiency of inducing a pluripotent stem cell is enhanced. In addition, it was thought that, by using a virus solution by dilution when gene transfer with Retronectin is carried out, a gene transfer efficiency is enhanced and, as a result, it is possible to further enhance an efficiency of inducing a pluripotent stem cell.

Example 10

Study of Gene Transfer Methods-2

Regarding gene transfer with a retrovirus vector, an amount of retrovirus was further changed in the condition under which each of Retronectin or polybrene was used, and induction of a pluripotent stem cell was carried out, followed by comparison.
(1) Immobilization of Retronectin on a Culture Plate
According to the same manner as that of Example 1-(1), immobilization of Retronectin on a culture plate was carried out.
(2) Gene Transfer with a Retrovirus Vector, First Time
According to the same manner as that of Example 7-(2), gene transfer was carried out, provided that a group in which a virus solution is diluted 10-fold or 100-fold with 10F-DMEM was set.
(3) Gene Transfer with a Retrovirus Vector, Second Time
According to the same manner as that of Example 7-(3), gene transfer for the second time was carried out, provided that, regarding a virus-diluted group, a virus solution diluted as in Example 10-(2) was used.
(4) Seeding on a Feeder Cell
According to the same manner as that of Example 7-(4), the gene-introduced cell was seeded on a feeder cell, and culturing was continued, provided that the gene-introduced cell was seeded by each $2 \times 10^4$ cells.
(5) Culturing
On the seventh day of culture (after culturing for 1 day from seeding on the feeder cell), the supernatant was removed from a 6-well culture plate, 2 mL of a medium for ES cells was added, and culturing was continued until the 28th day of culture. During this, the medium was exchanged at 1 to 2 days interval.
(6) Counting of a Pluripotent Stem Cell Colony
On the 28th day of culture, the number of a pluripotent stem cell (iPS cell) colony under each condition was counted. The results thereof are shown in Table 17. In addition, the number in the Table indicates an average value of N=2.

TABLE 17

Numbers of iPS cell colonies on the 28th day of culture

| Gene transfer method | Number of iPS cell colonies |
| --- | --- |
| Gene transfer with Retronectin | 6.5 |
| Gene transfer with polybrene | 0.0 |
| Gene transfer with Retronectin, virus 10-fold dilution | 12.0 |
| Gene transfer with polybrene, virus 10-fold dilution | 1.5 |
| Gene transfer with Retronectin, virus 100-fold dilution | 17.5 |
| Gene transfer with polybrene, virus 100-fold dilution | 0.0 |

As shown in Table 17, by performing gene transfer with Retronectin, an efficiency of inducing a pluripotent stem cell was considerably higher than gene transfer with polybrene. In addition, it was revealed that, by using a virus solution by dilution when gene transfer with Retronectin is carried out, a gene transfer efficiency is further enhanced and, as a result, an efficiency of inducing a pluripotent stem cell is further enhanced.

Example 11

Study of Gene Transfer Methods-3

By limiting a gene to be introduced to three kinds of OCT4, SOX2 and KLF4, the same experiment as that of Example 10 was carried out.
(1) Immobilization of Retronectin on a Culture Plate
According to the same manner as that of Example 1-(1), immobilization of Retronectin on a culture plate was carried out.
(2) Gene Transfer with a Retrovirus Vector, First Time
According to the same manner as that of Example 10-(2), gene transfer was carried out, provided that, as the retrovirus vector, retrovirus vectors DON5-am-OCT4-IR-SOX2 and DON5-am-KLF4 prepared in Preparation Example 2 were used.
(3) Gene Transfer with a Retrovirus Vector, Second Time
According to the same manner as that of Example 10-(3), gene transfer for the second time was carried out, provided that the retrovirus vector used was the same as that of Example 11-(2).
(4) Seeding on a Feeder Cell
According to the same manner as that of Example 10-(4), the gene-introduced cell was seeded on a feeder cell, and culturing was continued.
(5) Culturing
Culturing was carried out according to the same manner as that of Example 10-(5).
(6) Counting of Pluripotent Stem Cell Colonies
On the 28th day of culture, the number of a pluripotent stem cell (iPS cell) colony under each condition was counted. The results thereof are shown in Table 18. In addition, the number in the Table indicates an average value of N=2.

TABLE 18

Numbers of iPS cell colonies on the 28th day of culture

| Gene transfer method | Number of iPS cell colonies |
| --- | --- |
| Gene transfer with Retronectin | 13.0 |
| Gene transfer with polybrene | 5.5 |
| Gene transfer with Retronectin, virus 10-fold dilution | 28.0 |
| Gene transfer with polybrene, virus 10-fold dilution | 6.0 |

TABLE 18-continued

Numbers of iPS cell colonies on the 28th day of culture

| Gene transfer method | Number of iPS cell colonies |
|---|---|
| Gene transfer with Retronectin, virus 100-fold dilution | 32.0 |
| Gene transfer with polybrene, virus 100-fold dilution | 4.0 |

As shown in Table 18, even when only three kinds of genes of OCT4, SOX2 and KLF4 were introduced, an efficiency of inducing a pluripotent stem cell was considerably higher by performing gene transfer with Retronectin than by performing gene transfer with polybrene. In addition, by using a virus solution by dilution when gene transfer with Retronectin is carried out, a gene transfer efficiency is further improved and, as a result, an efficiency of inducing a pluripotent stem cell becomes further high, and this is also true in the case of introduction of only three genes.

Example 12

Comparison of Gene Transfer Methods at Multiple Genes Introduction-3

Gene transfer efficiencies using a plurality of retrovirus vectors with Retronectin or polybrene were further compared. Introduction of a fluorescent protein gene was carried out targeting human skin fibroblast derived from four different donors, using a method of performing gene transfer two times as in the pluripotent stem cell inducing experiment. In the present Example, the cell A indicates derived from a 28 year-old Caucasian female, the cell B indicates derived from a 42 year-old Caucasian female, the cell C indicates derived from a 51 year-old Caucasian female, and the cell D indicates derived from a 48 year-old African-American female (all manufactured by Lonza).

(1) Immobilization of Retronectin on a Culture Plate

According to the same manner as that of Example 8-(1), immobilization of Retronectin on a culture plate was carried out.

(2) Gene Transfer with a Retrovirus Vector, First Time

According to the same manner as that of Example 8-(2), gene transfer was carried out (day 0 of culturing), provided that a group in which a virus solution was diluted 10-fold, 100-fold or 1000-fold with 10F-DMEM was set.

(3) Gene Transfer with a Retrovirus Vector, Second Time

Gene transfer for the second time was carried out on the first day of culture, according to the same manner as that of Example 12-(2), provided that, in gene transfer with polybrene, the supernatant was removed on the second day of culture, 500 µL of 10F-DMEM was added, and culturing was continued.

(4) Measurement of Gene Transfer Efficiencies

According to the same manner as that of Example 8-(3), a gene transfer efficiency was measured on the sixth day of culture. The results thereof are shown in Table 19. Table 19 shows a ratio of both positive cells in each cell, in each gene transfer method. In addition, the number in the Table indicates an average value of N=2.

TABLE 19

Ratio of double positive cells

| Gene transfer method | Cell A | Cell B | Cell C | Cell D |
|---|---|---|---|---|
| Retronectin, Virus stock solution | 42.5 | 35.9 | 42.1 | 38.4 |
| Polybrene, Virus stock solution | 17.9 | 16.3 | 17.1 | 16.5 |
| Retronectin, Virus 10-fold dilution | 55.9 | 49.7 | 54.6 | 54.2 |
| Polybrene, Virus 10-fold dilution | 40.1 | 39.2 | 36.0 | 44.1 |
| Retronectin, Virus 100-fold dilution | 61.6 | 57.7 | 60.2 | 63.2 |
| Polybrene, Virus 100-fold dilution | 9.7 | 9.7 | 11.6 | 14.4 |
| Retronectin, Virus 1000-fold dilution | 51.9 | 48.7 | 46.4 | 51.0 |
| Polybrene, Virus 1000-fold dilution | 0.3 | 0.3 | 0.4 | 0.6 |

As shown in Table 19, it was first revealed that, in gene transfer using Retronectin, little influence of a donor of human adult skin fibroblast on a gene transfer efficiency is seen. That is, it is thought that stable gene transfer is possible regardless of an origin of a donor, when inducing a pluripotent stem cell using Retronectin.

By performing gene transfer in the presence of Retronectin upon gene transfer using two kinds of retrovirus vectors, a ratio of cells in which both genes were introduced was high, as compared with gene transfer with polybrene. That is, since when a pluripotent stem cell is induced, two or more kinds of retrovirus vectors are used in many cases, it is thought that, by using Retronectin upon the induction, a ratio of introduction of a plurality of genes is enhanced and, as a result, an efficiency of inducing a pluripotent stem cell is enhanced.

In addition, as shown in Table 19, even when a virus solution is used by diluting 100-fold or 1000-fold upon gene transfer with Retronectin, gene transfer with high efficiency becomes possible. That is, it is suggested that, by using Retronectin upon induction of a pluripotent stem cell, it is possible to induce a pluripotent stem cell with high induction efficiency even with a low titer virus or a small amount of virus.

Example 13

Study of Differences Between Donors

Regarding gene transfer with a retrovirus vector, a pluripotent stem cell was induced using Retronectin or polybrene, targeting four kinds of human adult skin fibroblasts as in Example 12, followed by comparison. The set conditions are shown in Table 20.

TABLE 20

| Condition | Treating method |
|---|---|
| Condition A | Gene transfer with Retronectin, Cell A |
| Condition B | Gene transfer with polybrene, Cell A |
| Condition C | Gene transfer with Retronectin, Cell B |
| Condition D | Gene transfer with polybrene, Cell B |
| Condition E | Gene transfer with Retronectin, Cell C |
| Condition F | Gene transfer with polybrene, Cell C |
| Condition G | Gene transfer with Retronectin, Cell D |
| Condition H | Gene transfer with polybrene, Cell D |

(1) Immobilization of Retronectin on a Culture Plate

According to the same manner as that of Example 1-(1), immobilization of Retronectin on a culture plate was carried out, provided that a non-treatment 12-well culture plate (manufactured by Becton, Dickinson and Company) was used, and each 1 mL of a Retronectin solution was added to each well.

(2) Gene Transfer with a Retrovirus Vector, First Time

According to the same manner as that of Example 7-(2), gene transfer was carried out (day 0 of culturing), provided that a 12-well plate for culturing a cell (manufactured by Corning) was used in gene transfer with polybrene. A virus solution was added to each well by each 1 mL by diluting 10-fold a solution obtained by mixing equal amounts of three kinds of vectors, with 10F-DMEM. Human adult skin fibroblast suspended in 10F-DMEM to $5 \times 10^4$ cells/mL was seeded on each well by each 1 mL.

(3) Gene Transfer with a Retrovirus Vector, Second Time

According to the same manner as that of Example 13-(2), gene transfer for the second time was carried out on the first day of culture, provided that, in gene transfer with polybrene, the supernatant was removed on the second day of culture, each 1 mL of 10F-DMEM was added, and culturing was continued.

(4) Seeding on a Feeder Cell

On the sixth day of culture, according to the same manner as that of Example 5-(4), the gene-introduced cell was seeded on a feeder cell, and culturing was continued.

(5) Culturing

According to the same manner as that of Example 10-(5), culturing on the feeder cell was carried out until the 25th day of culture.

(6) Counting of a Pluripotent Stem Cell Colony

On the 25th day of culture, the number of a pluripotent stem cell (iPS cell) under each condition was counted. The results thereof are shown in Table 21. In addition, the number in the Table indicates an average value of N=2.

TABLE 21

Numbers of iPS cell colonies on the 25th day of culture

| Condition | Number of iPS cell colonies |
| --- | --- |
| Condition A | 81.0 |
| Condition B | 22.0 |
| Condition C | 6.5 |
| Condition D | 3.0 |
| Condition E | 114.0 |
| Condition F | 22.0 |
| Condition G | 44.5 |
| Condition H | 12.5 |

As shown in Table 21, formation of a pluripotent stem cell was recognized in all conditions and, in any donor-derived cell, an efficiency of inducing a pluripotent stem cell was considerably higher by performing gene transfer with Retronectin than by performing gene transfer with polybrene.

Example 14

Study of Genes to be Introduced

Regarding gene transfer with a retrovirus vector, pluripotent stem cell induction was carried out using Retronectin by changing a combination of genes to be introduced, followed by comparison. The set combinations are shown in Table 22.

TABLE 22

Combinations of retrovirus vectors

| Condition A | DON5-am-OCT4-IR-SOX2 |
| --- | --- |
| | DON5-am-KLF4 |
| Condition B | DON5-am-OCT4-IR-SOX2 |
| | DON5-am-NANOG |
| Condition C | DON5-am-OCT4-IR-SOX2 |
| | DON5-am-LIN28 |
| | DON5-am-KLF4 |
| Condition D | DON5-am-OCT4-IR-SOX2 |
| | DON5-am-NANOG |
| | DON5-am-KLF4 |
| Condition E | DON5-am-OCT4-IR-SOX2 |
| | DON5-am-LIN28-IR-NANOG |
| | DON5-am-KLF4 |

(1) Immobilization of Retronectin on a Culture Plate

According to the same manner as that of Example 13-(1), immobilization of Retronectin on a culture plate was carried out.

(2) Gene Transfer with a Retrovirus Vector, First Time

According to the same manner as that of Example 4-(2), gene transfer was carried out. Each 1 mL of a virus solution was added to each well, by mixing equal amounts of respective solutions in a combination in Table 22, and diluting 100-fold with 10F-DMEM. Each 1 mL of human adult skin fibroblast suspended in 10F-DMEM to $5 \times 10^4$ cells/mL was seeded on each well.

(3) Gene Transfer with a Retrovirus Vector, Second Time

According to the same manner as that of Example 14-(2), gene transfer for the second time was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Culturing

According to the same manner as that of Example 10-(5), culturing on the feeder cell was carried out until the 25th day of culture.

(6) Counting of Pluripotent Stem Cell Colonies

On the 25th day of culture, the number of a pluripotent stem cell (iPS cell) colony under each condition was counted. The results thereof are shown in Table 23. In addition, the number in the Table indicates an average value of N=4.

TABLE 23

Numbers of iPS cell colonies on the 25th day of culture

| Condition | Number of iPS cell colonies |
| --- | --- |
| Condition A | 28.3 |
| Condition B | 2.0 |
| Condition C | 82.5 |
| Condition D | 41.8 |
| Condition E | 84.3 |

As shown in Table 23, even in combinations of various genes, formation of a pluripotent stem cell was recognized by using Retronectin.

Example 15

Establishment of a Pluripotent Stem Cell Clone

Pluripotent stem cell (iPS cell) colonies induced by gene transfer using Retronectin were picked up, and iPS cell clones for use in various assays were established.

(1) Immobilization of Retronectin on a Culture Plate

According to the same manner as that of immobilization of Retronectin on a culture plate was carried out.

(2) Gene Transfer with a Retrovirus Vector, First Time

According to the same manner as that of Example 2-(2), gene transfer was carried out.

(3) Gene Transfer with a Retrovirus Vector, Second Time

According to the same manner as that of Example 2-(3), gene transfer for the second time was carried out.

(4) Seeding on a Feeder Cell

According to the same manner as that of Example 2-(4), seeding of the gene-introduced cell on a feeder cell was carried out, provided that the gene-introduced cell was seeded by each $4 \times 10^5$ cells.

(5) Culturing

On the seventh day of culture (after culturing for 1 day from seeding on the feeder cell), the supernatant was removed from a petri dish, and culturing thereafter was carried out under control condition (a medium for ES cells) or protein starvation treatment condition (after culturing with 0F-DMEM for 2 days, the medium was exchanged with a medium for an ES medium). After exchange of the medium, culturing under each condition was continued until the 29th day of culture and, during this, the medium was exchanged at 1 to 2 days interval.

(6) Selection

A pluripotent stem cell (iPS cell) colony formed on a 10 cm petri dish under each condition on the 29th day of culture was picked up under a stereomicroscope (SZ61; manufactured by Olympus Corporation). The picked up iPS cell colonies were transferred to wells of a 96-well culture plate to which 100 µL of a medium for ES cells had been added in advance, pipetting was carried out several times, the colonies were subcultured onto a 24-well culture plate on which a feeder cell had been seeded by each $5.4 \times 10^4$ cells per well. After subculturing, medium exchange was carried out everyday, an iPS cell colony which became a sufficient size was arbitrarily subcultured, thereby, an iPS cell clone was established. In addition, as an iPS cell clone obtained by performing protein starvation treatment, clones #1, #4, #5, #6 and #10 were established, and a clone #3 was established as an iPS cell clone under control condition.

Example 16

Quantitation of a Copy Number of a Provirus Inserted into a Genome of an iPS Cell Clone Quantitation of a copy number of a provirus inserted into a genome of an iPS cell clone was carried out. As a control, an iPS cell clone established in Kyoto University "253G1" [Nakagawa, M. et al., Nat. Biotechnol.], vol. 26, No. 1, pp. 11-106, 2008] was similarly analyzed.

(1) Genome Extraction

Each confluent iPS cell clone (clone #1, #3, #4, #5, #6, or #10) established in Example 15, or 253G1 was recovered with ES cells peeling solution into one well of a 6-well plate, and genome extraction was carried out using PUREGENE DNA Purification Kit (manufactured by QIAGEN).

(2) Real Time PCR

A copy number of a provirus inserted into a genome of an iPS cell clone was calculated by real time PCR using Cycleave PCR Core Kit (manufactured by TAKARA BIO INC.). Using a primer set and a DNA control template attached to Provirus Copy Number Detection Primer Set, Human (for Real Time PCR) (manufactured by TAKARA BIO INC.), a provirus copy number and a human IFNγ copy number per 200 ng of a genome DNA extracted in Example 16-(1) were calculated, respectively, and an inserted retrovirus copy number per one cell was calculated by (retrovirus copy number)/(human IFNγ copy number)×2. In addition, all were carried out by N=2, and an average was calculated.

As a result, 253G1 as a control was about 19.3 copies, the clone #1 was about 6.4 copies, the clone #3 was about 10.2 copies, the clone #4 was about 7.1 copies, the clone #5 was about 11.4 copies, the clone #6 was about 5.7 copies, and the clone #10 was about 13.3 copies. From this, gene transfer with Retronectin was carried out using a retrovirus made based on pDON-5 vector, and it could be confirmed that, in all of made iPS cell clones, although a retrovirus inserted copy number is apparently smaller than 253G1 which was gene-introduced using polybrene and made, an iPS cell can be made more effectively by the aforementioned method.

Example 17

Confirmation of Expression of ES Cell Marker Genes

Whether the established each iPS cell clone expresses a marker gene of ES cells or not was confirmed by RT-PCR. In addition, the iPS cell clone of the clone #1, the clone #3, and the iPS cell clone of 253G1 as a control were confirmed.

(1) RNA Extraction

Several tens colonies of each iPS cell colony were recovered, and a total RNA was recovered by FastPure (registered trademark) RNA Kit (manufactured by TAKARA BIO INC.). A method was followed by a protocol of extraction of a total RNA from a cultured cell attached to the Kit.

(2) Synthesis of a cDNA

Employing a total RNA extracted in Example 17-(1), synthesis of a cDNA was carried out. Using PrimeScript (registered trademark) RT Reagent Kit (Perfect Real Time) (manufactured by TAKARA BIO INC.), a premix was prepared according to a protocol in the case of SYBR Green Assay, and 200 ng of a total RNA was added. Using TAKARA PCR Thermal Cycler Dice Gradient (manufactured by TAKARA BIO INC.), a reaction was carried out at 37° C. for 15 minutes, and at 85° C. for 5 seconds to obtain a cDNA.

(3) PCR Reaction

First, synthetic primers having nucleotide sequences described in Sequence Listing SEQ ID Nos.: 7 to 10, and a synthetic primer having a nucleotide sequence described in Reference Publication [Takahashi, K et al., Cell, vol. 131, pp. 861-872, 2007] were synthesized with a DNA synthesizer, and purified by the conventional method.

Among the cDNA obtained in Example 17-(2), a 20 ng portion in terms of a total RNA amount was used as a template to perform PCR. 5 µL of 5× PrimeSTAR GXL Buffer (manufactured by TAKARA BIO INC.), 2 µL of dNTP Mixture (2.5 mM each) (manufactured by TAKARA BIO INC.), 5 µmol of a forward primer, 5 pmol of a reverse primer and 0.5 µL of PrimeSTAR (registered trademark) GXL DNA Polymerase (1.25 U/µL) (manufactured by TAKARA BIO INC.) were added, and sterile distilled water was added to a total amount of 25 µL. The reaction solution was set in TaKaRa PCR Thermal Cycler Dice Gradient, and a reaction of 30 cycles was carried out, one cycle being 10 seconds at 98° C., 15 seconds at 60° C., and 15 seconds at 68° C.

(4) Confirmation by Agarose Gel Electrophoresis

After completion of the reaction, 5 µL of the reaction solution was subjected to 3.0% agarose gel electrophoresis, and an amplified DNA fragment was confirmed. The results are shown in FIG. 1. As apparent from FIG. 1, each ES cell marker which is not confirmed in original human adult skin fibroblast (NHDF-Ad) was confirmed in the clone #1, the clone #3 and 253G1. That is, it was confirmed that the established iPS cell clone exhibits the same gene expression pattern as that of ES cells.

Example 18

In Vivo Assessment of Pluripotency of an iPS Cell Clone

In order to confirm that the established iPS cell clone has pluripotency like a human ES cell, the clone #1 was transplanted into a testis of the SCID mouse, and the teratoma forming ability was assessed.

(1) Preparation of an iPS Cell Suspension

The cultured iPS cell clone (clone #1) was recovered using an ES cell peeling solution (20% Knockout Serum Replacement, 1 mM $CaCl_2$, 0.1 mg/mL collagenase IV, 0.25% trypsin), and cell counting was carried out using a portion of it. After the iPS cell suspension was centrifuged, the supernatant was removed, and the cells were adjusted to $5\times10^6$ cells/mL with HANKS' BALANCED SALT SOLUTION (manufactured by Sigma).

(2) Administration of an iPS Cell Suspension to a Testis of the SCID Mouse

The iPS cell suspension prepared in Example 18-(1) was administered to a testis of the SCID mouse at $2.5\times10^5$ cells/50 µL.

(3) Preparation of a Frozen Section of a Formed Teratoma

Figure 2:
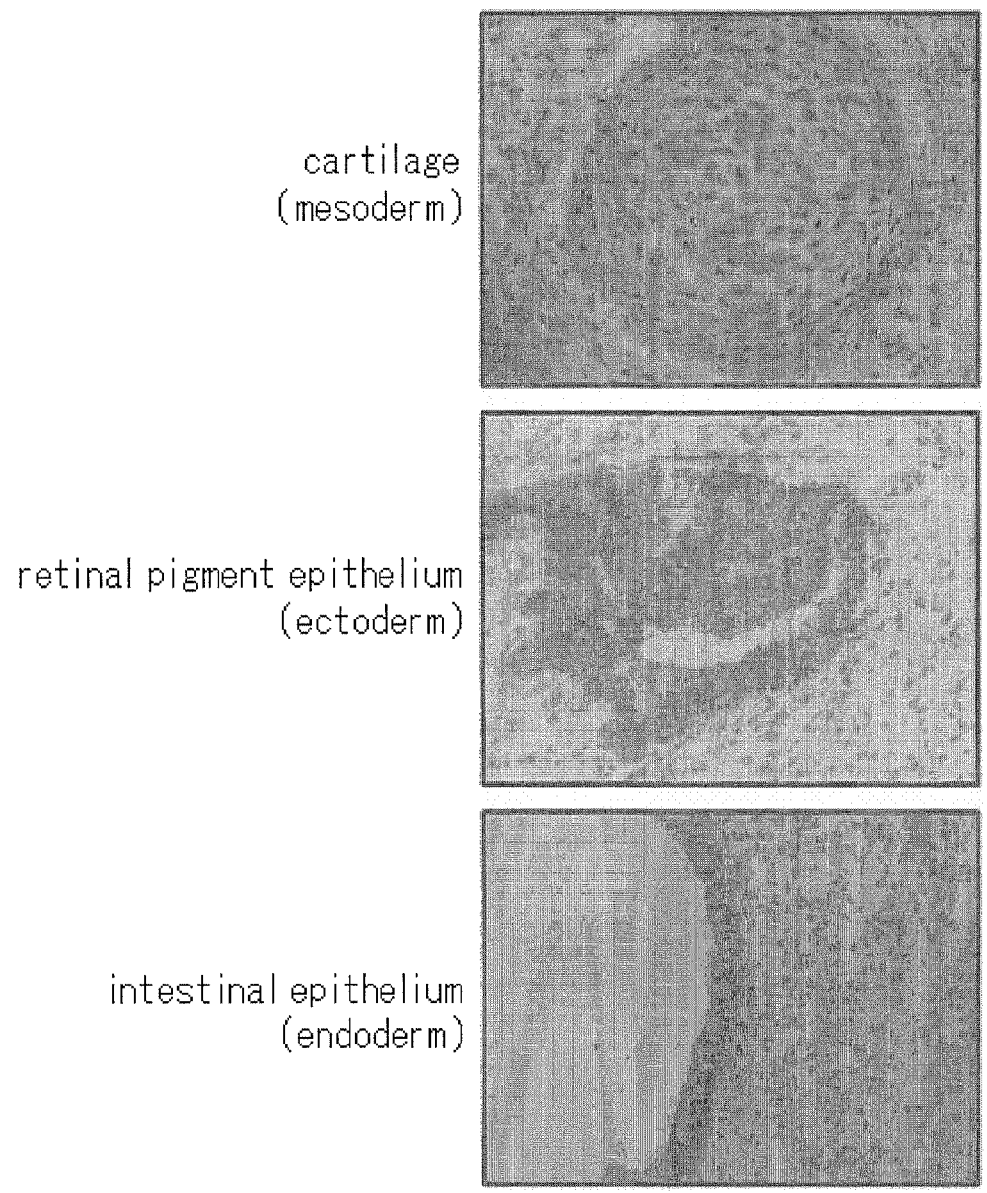
FIG. 2 is a photograph of cells derived from triploblast exhibiting the ability to form a teratoma of the established iPS cell clone.

After administration of the iPS cell, necropsy was carried out in $10^{th}$ week, a teratoma was taken out from the SCID mouse, and embedded in TISSUE MOUNT (manufactured by Chiba Medical) to make a frozen block. The frozen block was stored at −80° C. until use. A frozen section was made using a cryostat, and HE-stained by a standard method, and microscopic examination was carried out. The results thereof are shown in FIG. 2. Since a tissue derived from triploblast could be observed as shown in FIG. 2, the iPS cell clone established by gene transfer with Retronectin was assessed to have pluripotency.

Example 19

Comparison of Gene Transfer Efficiencies in Each Gene Transfer Method and a Pluripotent Stem Cell (iPS cell) Colony Number As an index showing an existence rate of a cell in which each retrovirus vector together with a gene encoding a nuclear reprogramming factor (iPS cell inducing factor) was inserted, gene transfer of an AcGFP1 gene was carried out, and a pluripotent stem cell (iPS cell) induction efficiency and an AcGFP1 positive cell rate, in a gene transfer method with Retronectin (Retronectin method) and a gene transfer method with polybrene (polybrene method) were compared. In addition, regarding partial condition, quantitation of a copy number of a retrovirus vector inserted into a genome was carried out, and comparison of a copy number and a pluripotent stem cell (iPS cell) induction efficiency was carried out.

(1) Immobilization of Retronectin on a Culture Plate

According to the same manner as that of Example 1-(1), immobilization of Retronectin on a culture plate was carried out, provided that, for a plate coated with Retronectin, a non-treatment 12-well plate was used, and each 1 mL of a Retronectin solution (25 µg/mL) was added to each well.

(2) Gene Transfer with a Retrovirus Vector, First Time

The virus solutions prepared in Preparation Example 2 and Preparation Example 3 were mixed at an equal amount in a combination of Table 24, the solution in which the virus solution was diluted 10-fold and 100-fold with 10F-DMEM was prepared regarding the condition A, and the solution in which the virus solution was diluted 10-fold was prepared regarding the condition B, and these were used in gene transfer. Gene transfer was carried out according to the same manner as that of Example 7-(2), provided that 1 mL of PSB was used for washing a plate with PBS in the Retronectin method, the cell number used in infection by the Retronectin method and the polybrene method was $4\times10^4$ cells/well, and a retrovirus vector solution was 1 mL/well.

TABLE 24

| Combinations of retrovirus vectors | |
|---|---|
| Condition A | DON5-am-OCT4-IR-SOX2 |
| | DON5-am-LIN28-IR-NANOG |
| | DON5-am-KLF4 |
| | DON-am-AcGFP1 |
| Condition B | DON5-am-OCT4-IR-SOX2 |
| | DON5-am-KLF4 |
| | DON-am-AcGFP1 |

(3) Gene Transfer with a Retrovirus Vector, Second Time

According to the same manner as that of Example 19-(2), gene transfer for the second time was carried out on the first day of culture.

(4) Seeding on a Feeder Cell and Measurement of an AcGFP1 Positive Cell Rate

According to the same manner as that of Example 10-(4), seeding of the gene-introduced cell on a feeder cell was carried out, provided that an AcGFP1 positive cell rate was measured with a flow cytometer using remaining cells which were not used in seeding on the feeder cell.

(5) Culturing

According to the same manner as that of Example 10-(5), culturing on the feeder cell was carried out, provided that cells were recovered from a part of wells under the condition A on the 11th day of culture, genome extraction was carried out, and the inserted number of the retrovirus vector was quantitated.

(6) Counting of Pluripotent Stem Cell (iPS Cell) Colonies

On the 28th day of culture, the number of a pluripotent stem cell (iPS cell) colony under each condition was counted.

The results of Example 19-(4), (5) and (6) are shown in Table 25.

TABLE 25

Results of an AcGFP1 positive rate, an inserted copy number, and an iPS cell colony number under each condition

| Condition | Virus dilution rate | Infection method | AcGFP1 positive rate | Inserted copy number | iPS cell colony number |
|---|---|---|---|---|---|
| Condition A | 10-fold dilution | Retronectin method | 82.8 | 5.2 | 10.0 |
| Condition A | 10-fold dilution | Polybrene method | 83.6 | 4.1 | 3.0 |
| Condition A | 100-fold dilution | Retronectin method | 94.1 | 7.8 | 27.0 |
| Condition A | 100-fold dilution | Polybrene method | 36.7 | 1.2 | 0.0 |

TABLE 25-continued

Results of an AcGFP1 positive rate, an inserted copy number,
and an iPS cell colony number under each condition

| Condition | Virus dilution rate | Infection method | AcGFP1 positive rate | Inserted copy number | iPS cell colony number |
|---|---|---|---|---|---|
| Condition B | 10-fold dilution | Retronectin method | 88.0 | Not tested | 11.5 |
| Condition B | 10-fold dilution | Polybrene method | 88.0 | Not tested | 4.5 |

As shown in Table 25, a difference in the iPS cell colony was recognized even in the condition under which there is little difference in the AcGFP1 positive rate and the inserted copy number. Specifically, under the condition of retrovirus 10-fold dilution of the condition A, there is no difference in the AcGFP positive rate between the Retronectin method and the polybrene method and, irrespective of the result that the Retronectin method is more only by 0.9 copy in the inserted copy number, a difference of 3-fold or more was recognized in the iPS cell colony number. In addition, when Retronectin method 100-fold dilution and polybrene method 10-fold dilution of the condition A were compared, the inserted copy number is about 2-fold higher in the Retronectin method, but the iPS cell colony number indicated a considerably higher value which is 9-fold. Although there is no difference in the AcGFP1 positive rate in both methods also regarding the condition B, the iPS cell colony number was 2-fold higher value in the Retronectin method. From them, it is assured that a gene transfer efficiency is improved in the Retronectin method, but a high pluripotent stem cell induction efficiency which can be explained only by them with difficulty is exhibited, and it was first revealed that Retronectin has the function of enhancing a pluripotent stem cell induction efficiency in addition to the function of enhancing a gene transfer efficiency.

Example 20

Study of Differences Between Retrovirus Vector Preparation Lots

Using five kinds of retrovirus vectors having different production lots obtained by a series of preparation operations of five times (hereinafter, expressed as virus 1 to 5, respectively), gene transfer with Retronectin was carried out, and a pluripotent stem cell induction efficiency was compared. The virus 1 was subjected to an experiment as it was immediately after preparation and recovery, and the viruses 2 to 5 were frozen and stored after preparation, and thawed viruses were subjected to an experiment.

(1) Immobilization of Retronectin on a Culture Plate

According to the same manner as that of Example 1-(1), immobilization of Retronectin on a culture plate was carried out.

(2) Gene Transfer with a Retrovirus Vector, First Time

According to the same manner as that of Example 4-(2), gene transfer was carried out (day 0 of culturing), provided that the virus solution was added to each well by each 2 mL, by diluting a solution obtained by mixing equal amounts of three kinds of vectors 10-fold with 10F-DMEM.

(3) Gene Transfer with a Retrovirus Vector, Second Time

According to the same manner as that of Example 20-(2), gene transfer was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Culturing

According to the same manner as that of Example 10-(5), culturing on the feeder cell was carried out until the 25th day of culture.

(6) Counting of Pluripotent Stem Cell Colonies

On the 25th day of culture, the number of a pluripotent stem cell (iPS cell) colony was counted. The results thereof are shown in Table 26. In addition, the number in the Table indicates an average value of N=2.

TABLE 26

Numbers of iPS cell colonies on the 25th day of culture

| Condition | Number of iPS cell colonies |
|---|---|
| Virus 1 (unfrozen) | 34.5 |
| Virus2 (frozen and melted) | 32.5 |
| Virus3 (frozen and melted) | 38.0 |
| Virus4 (frozen and melted) | 33.5 |
| Virus5 (frozen and melted) | 33.5 |

As shown in Table 26, in pluripotent stem cell induction, little influence due to a production lot of a virus vector is seen. In addition, also when a virus vector used after freezing and storage, and thawing is used, the colony number equivalent to that of unfrozen was seen. It was revealed that, when a pluripotent stem cell is induced using Retronectin, it is possible to stably induce a pluripotent stem cell, regardless of some variation in a titer of the virus solution, and with or without freezing and melting.

Example 21

Comparison of Retronectin and Native Fibronectin in Gene Transfer by a Standing Infecting Method Using a plate coated with Retronectin and a plate coated with Native fibronectin, gene transfer was carried out, and pluripotent stem cell induction was carried out. In addition, as the plate, a plate made in the following Example 21-(1), and a marketed product of a 35 mm petri dish coated with Retronectin in advance (T110A manufactured by TAKARA BIO INC.), and a marketed product of a 35 mm petri dish coated with Native fibronectin in advance (354457 manufactured by FALCON) were used.

(1) Immobilization of Retronectin on a Culture Plate

According to the same manner as that of Example 1-(1), immobilization of Retronectin on a culture plate was carried out, provided that, as a culturing container, a non-treatment 35 mm petri dish (manufactured by IWAKI CO., LTD.) was used. In addition, petri dishes coated with Retronectin and Native fibronectin in advance which are marketed products (hereinafter, also described as Retronectin dish and fibronectin dish) were not subjected to these immobilization operations.

(2) Gene Transfer with a Retrovirus Vector, First Time

The virus solutions prepared in Preparation Example 2 were mixed at an equal amount in a combination of Table 27, and diluted 10-fold with 10F-DMEM, each 2 mL was added to the Retronectin-immobilized culturing petri dish prepared in Example 21-(1), or the petri dish coated with Retronectin or Native fibronectin in advance, and this was allowed to stand in a $CO_2$ incubator at 32° C. for 4 to 6 hours.

TABLE 27

Combinations of retrovirus vectors

| | |
|---|---|
| Condition A | DON5-am-OCT4-IR-SOX2 |
| | DON5-am-KLF4 |
| Condition B | DON5-am-OCT4-IR-SOX2 |
| | DON5-am-LIN28-IR-NANOG |
| | DON5-am-KLF4 |

Thereafter, the supernatant was removed from each petri dish, the petri dish was washed with PBS once, each 2 mL of human adult skin fibroblast suspended in 10F-DMEM to $5×10^4$ cells/mL was seeded on each petri dish, and culturing was initiated in a $CO_2$ incubator at 37° C. (day 0 of culturing).

(3) Gene Transfer with a Retrovirus Vector, Second Time

According to the same manner as that of Example 21-(2), gene transfer was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Culturing

According to the same manner as that of Example 10-(5), culturing on the feeder cell was carried out until the 27th day of culture.

(6) Counting of Pluripotent Stem Cell Colonies

On the 27th day of culture, the number of a pluripotent stem cell (iPS cell) colony under each condition was counted. The results are shown in Table 28. In addition, the number in the Table indicates an average value of N=3.

TABLE 28

Numbers of iPS cell colonies on the 27th day of culture

| Retrovirus combination condition | Gene transfer method | Number of iPS cell colonies |
|---|---|---|
| Condition A | Retronectin (immobilized) | 52.0 |
| | Retronectin dish | 42.3 |
| | Fibronectin dish | 0.0 |
| Condition B | Retronectin (immobilized) | 97.3 |
| | Retronectin dish | 115.7 |
| | Fibronectin dish | 0.0 |

As shown in Table 28, also in the standing infecting method in which a centrifugation operation is not carried out upon adsorption of a virus onto Retronectin, it was possible to induce an iPS cell with Retronectin. To the contrary, with the Native fibronectin, a pluripotent stem cell colony could not be obtained at all, regardless of a combination of retroviruses. Predominance of Retronectin over Native fibronectin in iPS cell induction was revealed.

Example 22

Study of Virus Mixing Ratios

Aiming at improving a pluripotent stem cell induction efficiency, study on a maximum virus vector mixing ratio was carried out. In addition, as a gene used for induction, three kinds of OCT4, SOX2 and KLF4 were used.

(1) Immobilization of Retronectin on a Culture Plate

According to the same manner as that of Example 11-(1), immobilization of Retronectin on a culture plate was carried out.

(2) Gene Transfer with a Retrovirus Vector, First Time

According to the same manner as that of Example 11-(2), gene transfer was carried out, provided that, as shown in Table 29, a virus mixing ratio was changed. In addition, the gene transfer method was the Retronectin method, and the virus solution was used in infection by diluting 100-fold.

TABLE 29

Retrovirus vector mixing ratios

| Condition | DON5-am-OCT4-IR-SOX2:DON5-am-KLF4 |
|---|---|
| Condition A | 1:1 |
| Condition B | 1:2 |
| Condition C | 2:1 |

(3) Gene Transfer with a Retrovirus Vector, Second Time

According to the same manner as that of Example 22-(2), gene transfer for the second time was carried out on the first day of culture.

(4) Seeding on a Feeder Cell

According to the same manner as that of Example 11-(4), the gene-introduced cell was seeded on a feeder cell, and culturing was continued.

(5) Culturing

According to the same manner as that of Example 10-(5), culturing on the feeder cell was carried out.

(6) Counting of Pluripotent Stem Cell Colonies

On the 27th day of culture, the number of a pluripotent stem cell (iPS cell) under each condition was counted. The results are shown in Table 30. In addition, the number in the Table indicates an average value of N=3.

TABLE 30

Numbers of iPS cell colonies under each condition

| Condition | Number of iPS cell colonies |
|---|---|
| Condition A | 10.0 |
| Condition B | 12.0 |
| Condition C | 19.3 |

As shown in Table 30, an iPS cell induction efficiency is dramatically increased by using a virus solution obtained by mixing DON5-am-OCT4-IR-SOX2 at an amount which is 2-fold an amount of DON5-am-KLF4, and it was revealed that an iPS cell induction efficiency can be further enhanced by optimizing a virus mixing ratio.

Example 23

An Efficiency of Introducing a Retrovirus Vector into Mouse Embryonic Fibroblast; MEF An efficiency of introducing a gene into MEF using a retrovirus vector was compared between a Retronectin method and a polybrene method.

(1) Immobilization of Retronectin on a Culture Plate

According to the same manner as that of Example 1-(1), immobilization of Retronectin on a culture plate was carried out, provided that, as a plate on which Retronectin is coated, a non-treatment 12-well plate (manufactured by Becton, Dickinson and Company) was used, and each 1 mL of a Retronectin solution (25 µg/mL) was added to each well.

(2) Gene Transfer with a Retrovirus Vector

According to the same manner as that of Example 19-(2) and (3), gene transfer was carried out. The retrovirus vector was prepared according to the same manner as that of Preparation Example 3, and DON-eco-AcGFP1 made using pE-Eco plasmid (manufactured by TAKARA BIO INC.) in place of pE-Ampho plasmid was used. Each of the prepared retrovirus vector as a stock solution, and solutions obtained by diluting the stock solution by each 10-fold to 100000-fold with 10F-DMEM was used for infection. In addition, as a target cell, MEF (manufactured by Millipore) was used.

(3) Medium Exchange

On the next day of gene transfer, the medium was exchanged with 10F-DMEM.

(4) Measurement of a Gene Transfer Efficiency

Four days after a gene transfer operation, the cells were recovered, and an AcGFP1 positive cell rate was measured with a flow cytometer. The results thereof are shown in Table 31.

TABLE 31

Comparison of infection efficiencies

| Gene transfer method | Virus concentration | Positive cell rate (%) |
|---|---|---|
| Gene transfer with Retronectin | 1.0 | 84.1 |
| | 0.1 | 80.3 |
| | 0.01 | 64.6 |
| | 0.001 | 41.3 |
| | 0.0001 | 15.3 |
| | 0.00001 | 5.9 |
| Gene transfer with polybrene | 1.0 | 54.6 |
| | 0.1 | 56.0 |
| | 0.01 | 26.7 |
| | 0.001 | 6.6 |
| | 0.0001 | 1.5 |
| | 0.00001 | 0.6 |

As shown in Table 31, a gene transfer efficiency by the Retronectin method was considerably higher than a gene transfer efficiency by the polybrene method. This demonstrates that the gene transfer method by the Retronectin method is effective on mouse fibroblast like human fibroblast, and it was suggested that effective induction of an iPS cell can be promoted.

Example 24 iPS Cell Induction from MEF Using Human iPS Cell Inducing Factors

An amino acid sequence of an iPS cell inducing factor is very similar between a human and a mouse, and it is presumed that the function is highly conserved. Then, whether a mouse iPS cell can be induced from MEF using a human iPS cell inducing factor or not was studied.

(1) Immobilization of Retronectin on a Culture Plate

According to the same manner as that of Example 1-(1), immobilization of Retronectin on a culture plate was carried out.

(2) Gene Transfer with Retrovirus Vectors

Gene transfer was carried out by the same Retronectin method as that of Example 23-(2). A combination of retrovirus vectors used in induction is shown in Table 32. In addition, the retrovirus vector was prepared by the same manner as that of Preparation Example 2, and a retrovirus vector made using the pE-Eco plasmid in place of the pE-Ampho plasmid was used.

TABLE 32

| Combinations of retrovirus vectors | |
|---|---|
| Condition A | DON5-eco-OCT4-IR-SOX2 |
| | DON5-eco-LIN28-IR-NANOG |
| | DON5-eco-KLF4 |
| Condition B | DON5-eco-OCT4-IR-SOX2 |
| | DON5-eco-KLF4 |

(3) Medium Exchange

On the next day and the third day of gene transfer, the medium was exchanged with 10F-DMEM.

(4) Seeding on a Feeder Cell

According to the same manner as that of Example 10-(4), the gene-introduced cell was seeded on a feeder cell, and culturing was continued, provided that a subculturing day was the fourth day from gene transfer, and a group of seeding by each $2 \times 10^5$, $5 \times 10^4$ or $1 \times 10^4$ cells was set.

(5) Culturing

On the fifth day of culture (after culturing for 1 day from seeding on the feeding cell), the supernatant was removed from a 6-well culture plate, and 2 mL of the medium for a mouse ES cell prepared by Preparation Example 4 was added. Culturing was continued until the 19th day of culture. During this, the medium was exchanged at 1 to 2 days interval.

(6) Counting of Pluripotent Stem Cell Colonies

On the 19th day of culture, the number of a pluripotent stem cell (iPS cell) colony under each condition was counted. The results thereof are shown in Table 33. In addition, the number in the Table indicates an average value of N=2.

TABLE 33

| Condition | Seeded cell number | Number of iPS cell colonies |
|---|---|---|
| Condition A | $2 \times 10^5$ | 2.5 |
| | $5 \times 10^4$ | 1.5 |
| | $1 \times 10^4$ | 0.0 |
| Condition B | $2 \times 10^5$ | 3.0 |
| | $5 \times 10^4$ | 1.0 |
| | $1 \times 10^4$ | 0.0 |

As shown in Table 33, it was revealed that a mouse iPS cell can be induced also from MEF, by using a virus vector carrying a human iPS cell inducing factor. From this, it was seen that the iPS cell inducing system using Retronectin is useful not only in a human but also in a mouse.

Example 25

Confirmation of Pluripotency by Differentiation Induction Via EB (Embryoid Body) of iPS Cells As one of definitions of an iPS cell, pluripotency has been exemplified, and pluripotency can be confirmed in vitro by differentiation induction via EB. Then, an experiment was conducted for the purpose of assessing pluripotency of the made iPS cell.

(1) Suspended Cell Culture of an iPS Cell

According to the same manner as that of Example 15-(6) and using a feeder cell and a medium for ES cells, an iPS cell clone which had been cultured in a 6-well culture plate (clone #3) was recovered using an ES cell peeling solution, suspended in an EB forming medium (80% DMEM/F12, 20% Knockout Serum Replacement, 2 mM L-glutamine, 1×NEAA Mixture), and suspending-cultured in a non-treatment 6-well culture plate. In addition, medium exchange was carried out at other day interval.

(2) Adhesion onto a Gelatin-Coated Plate

On the eighth day of culture, all amount of EB was seeded on a 24-well plate which had been coated with gelatin on the previous day, EB was made to adhere to the plate, and culturing was carried out for 8 days. In addition, medium exchange was carried out every other day.

(3) Immunostaining

On the 16th day of culture, a cell was fixed with 4% paraformaldehyde at room temperature for 10 minutes, washed with PBS two times, and blocked by reacting with 1% BSA/PBS at room temperature for 1 hour. Thereafter, a solution obtained by 50-fold diluting Mouse anti-βIII-tublin antibody (manufactured by Millipore) or Mouse anti-α-smooth muscle actin antibody (manufactured by DAKO) with 1% BSA/PBS was added, and this was incubated at 4° C. overnight. On the next day, after washing with PBS three times, blocking was carried out by reacting with 1% BSA/PBS at room temperature for 1 hour. A solution obtained by 1000-fold diluting the Alexa Fluor 594 F(ab')$_2$ fragment of goat anti-mouse IgG (H+L) antibody (manufactured by Invitrogen) with 1% BSA/PBS was added, and this was incubated at 4° C. overnight. On the next day, after washing with PBS three times, observation with a fluorescent microscope was conducted.

Figure 3:
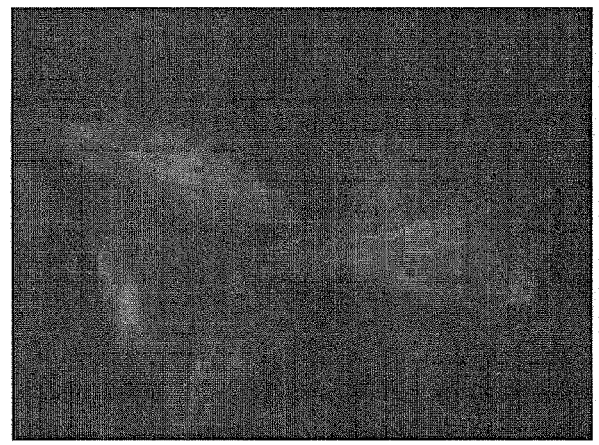
FIG. 3 is a photograph exhibiting pluripotency by differentiation induction of the established iPS cell clone via EB.
Figure 3:
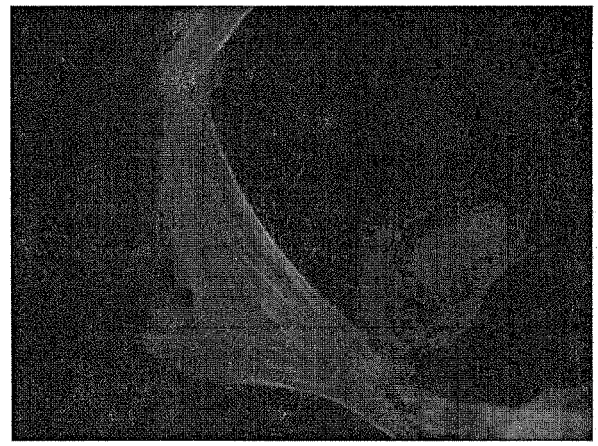

The results thereof are shown in FIG. 3. As apparent from FIG. 3, the iPS cell made by the present method can be differentiated into βIII-tublin positive cell which is an ectodermal cell, and into an α-smooth muscle action positive cell which is a mesodermal cell, and was demonstrated to have pluripotency.

Example 26

Study of Media from after Gene Transfer to Subculturing into a Feeder Cell

It was predicted that calf serum has a differentiation inducing factor at a smaller amount than that of FBS (bovine fetal serum), and a possibility that calf serum is more suitable for iPS cell induction was thought. Then, influence of a serum component in media used from after gene transfer to subculturing into a feeder cell on an iPS cell induction efficiency was studied.

(1) Immobilization of Retronectin on a Culture Plate

According to the same manner as that of Example 11-(1), immobilization of Retronectin on a culture plate was carried out.

(2) Gene Transfer with a Retrovirus Vector, First Time

According to the same manner as that of Example 11-(2), gene transfer was carried out using a solution which had been diluted 100-fold, by a Retronectin method.

(3) Gene Transfer with a Retrovirus Vector, Second Time

According to the same manner as that of Example 11-(3), gene transfer for the second time was carried out.

(4) Seeding on a Feeder Cell

According to the same manner as that of Example 11-(4), the gene-introduced cell was seeded on a feeder cell, and culturing was continued, provided that a serum component in the medium from the next day of second time gene transfer to seeding on a feeder cell was changed to a composition shown in Table 34.

TABLE 34

| Condition | Serum species (concentration) |
|---|---|
| Condition A | FBS (10%) |
| Condition B | Calf serum (2%) |
| Condition C | Calf serum (5%) |
| Condition D | Calf serum (10%) |
| Condition E | Calf serum (20%) |

(5) Culturing

According to the same manner as that of Example 10-(5), culturing on a feeder cell was carried out.

(6) Counting of Pluripotent Stem Cell Colonies

On the 27th day of culture, the number of a pluripotent stem cell (iPS cell) under each condition was counted. The results thereof are shown in Table 35. In addition, the number in the Table indicates an average value of N=2.

TABLE 35

| Condition | Number of iPS cell colonies |
|---|---|
| Condition A | 61.0 |
| Condition B | 48.0 |
| Condition C | 63.5 |
| Condition D | 72.5 |
| Condition E | 81.0 |

As shown in Table 35, an iPS cell induction efficiency was increased calf serum concentration-dependently, and a higher induction efficiency than that of the condition A which is a control group was obtained at 5%, 10% and 20%. From this, it was shown that calf serum is effective in extending a cell at iPS cell induction.

Example 27

Study of Cell Cycle Arresting Agent-2

Regarding Purvalanol A being a Cell cycle arresting agent, for which the effect of promoting induction of a pluripotent stem cell was confirmed in Example 3, extension of the substance treatment term thereof and a combination use thereof with Y-27632 [(R) (+)-trans-4-(1-aminoethyl)-N-(4-pyridyl) cyclohexanecarboxyamide dihydrochloride] which is one of substances suppressing cell death were studied.

(1) Immobilization of Retronectin on a Culture Plate

According to the same manner as that of Example 1-(1), immobilization of Retronectin on a culture plate was carried out.

(2) Gene Transfer with a Retrovirus Vector, First Time

According to the same manner as that of Example 3-(2), gene transfer was carried out (day 0 of culturing), provided that the virus solution was added to each well by each 2 mL, by diluting 10-fold a solution obtained by mixing three kinds of vectors at an equal amount, with 10F-DMEM.

(3) Gene Transfer with a Retrovirus Vector, Second Time

According to the same manner as that of Example 27-(2), gene transfer for the second time was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Cell Cycle Arresting Agent Treatment and Culturing

On the seventh day of culture (after culturing for 1 day from seeding on the feeder cell), the supernatant was removed from a 6-well culture plate, the medium was exchanged with a medium for ES cells, and substance treatment was carried out, as shown in Table 36. After completion of a substance treatment term, the medium was exchanged with a medium for ES cells, and culturing was continued until the 26th day of culture. During this, the medium was exchanged at 1 to 2 days interval. Regarding the condition under which substance treatment for 4 days to 6 days was carried out, the medium was exchanged at two days interval also during a substance treatment term, and the substance was added at the same concentration every time.

TABLE 36

Agent treatment conditions

| Condition | Treating method |
|---|---|
| Control | Exchange with a medium for ES cells |
| Condition A | Culturing for 2 days in a medium for ES cells containing 2 μM Purvalanol A |
| Condition B | Culturing for 4 days in a medium for ES cells containing 2 μM Purvalanol A |
| Condition C | Culturing for 6 days in a medium for ES cells containing 2 μM Purvalanol A |
| Condition D | Culturing for 2 days in a medium for ES cells containing 2 μM Purvalanol A and 10 μM Y27632 |
| Condition E | Culturing for 4 days in a medium for ES cells containing 2 μM Purvalanol A and 10 μM Y27632 |
| Condition F | Culturing for 6 days in a medium for ES cells containing 2 μM Purvalanol A and 10 μM Y27632 |

(6) Counting of Pluripotent Stem Cell Colonies

On the 26th day of culture, the number of a pluripotent stem cell (iPS cell) colony under each condition was counted. The results are shown in Table 37. In addition, the number in the Table indicates an average value of N=2.

TABLE 37

Numbers of iPS cell colonies on the 26th day of culture

| Condition | Number of iPS cell colonies |
|---|---|
| Control | 15.5 |
| Condition A | 26.0 |
| Condition B | 25.5 |
| Condition C | 18.5 |
| Condition D | 24.5 |
| Condition E | 36.0 |
| Condition F | 24.5 |

As shown in Table 37, it was revealed that an efficiency of inducing a pluripotent stem cell is further enhanced, by extending a substance treatment term with Purvalanol A to 4 days. In addition, it was revealed that, when a substance treatment term with Purvalanol A is extended, a pluripotent stem cell colony can be stably obtained by adding Y27632 which is one of substances suppressing cell death.

Example 28

Study of a Cell Cycle Arresting Agent-3

In induction culturing of a pluripotent stem cell, substance treatment with NU610 (manufactured by ALEXIS BIO-CHEMICALS) which is one of Cell cycle arresting agents was carried out, and influence on an induction efficiency was studied.

(1) Immobilization of Retronectin on a Culture Plate

According to the same manner as that of Example 1-(1), immobilization of Retronectin on a culture plate was carried out, provided that a non-treatment 12-well culture plate (manufactured by Becton, Dickinson and Company) was used, and each 1 mL of a Retronectin solution was added to each well.

(2) Gene Transfer with a Retrovirus Vector, First Time

According to the same manner as that of Example 4-(2), gene transfer was carried out (day 0 of culturing), provided that each 1 mL of the virus solution was added to each well, by diluting 100-fold a solution obtained by three kinds of vectors at an equal amount, with 10F-DMEM.

(3) Gene Transfer with a Retrovirus Vector, Second Time

According to the same manner as that of Example 28-(2), gene transfer for the second time was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Cell Cycle Arresting Treatment and Culturing

On the seventh day of culture (after culturing for 1 day from seeding on a feeder cell), the supernatant was removed from a 6-well culture plate, the medium was exchanged with a medium for ES cells, and groups to which NU6140 was added to a final concentration of 0.1 μM and 1 μM, respectively, were set. In addition, in a control, the substance was not added. After culturing for 2 days, the medium was exchanged with a medium for ES cells, and culturing was continued to the 28th day of culture. During this, the medium was exchanged at 1 to 2 days interval.

(6) Counting of Pluripotent Stem Cells

On the 28th day of culture, the number of a pluripotent stem cell (iPS cell) colony under each condition was counted. The results thereof are shown in Table 38. In addition, the number in the Table indicates an average value of N=2.

TABLE 38

Numbers of iPS cell colonies on the 28th day of culture

| Condition | Number of iPS cell colonies |
|---|---|
| Control | 21.5 |
| NU6140 0.1 μM | 22.5 |
| NU6140 1 μM | 28.0 |

As shown in Table 38, the number of a pluripotent stem cell became larger in a group of substance treatment with NU6140 than in a control (non-treated). That is, it was reconfirmed that an induction efficiency is enhanced by arresting cell cycle in a process of inducing a pluripotent stem cell.

Example 29

Study of DHCP

In induction culturing of a pluripotent stem cell, substance treatment with a compound DHCP produced by heating a uronic acid compound derived from an animal and a plant (International Publication No. 98/13328 pamphlet), and GM in which glutathione is added to DHCP (International Publication No. 98/39291 pamphlet) was carried out, and influence on an induction efficiency was studied.

(1) Immobilization of Retronectin on a Culture Plate

According to the same manner as that of Example 28-(1), immobilization of Retronectin on a culture plate was carried out.

(2) Gene Transfer with a Retrovirus Vector, First Time

According to the same manner as that of Example 4-(2), gene transfer was carried out (day 0 of culturing), provided that each 1 mL of the virus solution was added to each well, by diluting 10-fold a solution obtained by three kinds of vectors at an equal amount, with 10F-DMEM.

(3) Gene Transfer with a Retrovirus Vector, Second Time

According to the same manner as that of Example 28-(2), gene transfer for the second time was carried out on the first day of culture.

(4) Seeding on a Feeder Cell

On the sixth day of culture, according to the same manner as that of Example 5-(4), the gene-introduced cell was seeded on a feeder cell, and culturing was continued.

(5) Agent Treatment and Culturing

On the seventh day of culture (after culturing for 1 day from seeding on a feeder cell), the supernatant was removed from a 6-well culture plate, the medium was exchanged with a medium for ES cells, and groups to which DHCP and GM was added to a final concentration of 10 µM, respectively, were set. In addition, in a control, the substance was not added. After culturing for 2 days, the medium was exchanged with a medium for ES cells, and culturing was continued to the 28th day of culture. During this, the medium was exchanged at 1 to 2 days interval.

(6) Counting of Pluripotent Stem Cell Colonies

On the 26th day of culture, the number of a pluripotent stem cell (iPS cell) colony under each condition was counted. The results thereof are shown in Table 39. In addition, the number in the Table indicates an average value of N=2.

TABLE 39

Numbers of iPS cell colonies on the 26th day of culture

| Condition | Number of iPS cell colonies |
|---|---|
| Control | 14.0 |
| DHCP 10 µM | 23.5 |
| GM 10 µM | 18.5 |

As shown in Table 39, the number of a pluripotent stem cell colony became larger in groups of substance treatment with DHCP and GM than in a control (non-treated). That is, it was revealed that DHCP and GM which is a derivative thereof have the effect of promoting a pluripotent stem cell.

Example 30

Comparison Between Retronectin and Native Fibronectin in Gene Transfer by a Standing Infecting Method-2

As in Example 21, gene transfer was carried out using a plate coated with Retronectin and a plate coated with Native fibronectin, and pluripotent stem cell induction was carried out. At the same time, gene transfer with polybrene was carried out, and a dilution rate of a virus solution was also studied. In addition, as a plate used, a marketed product of a 35 mm petri dish coated with Retronectin in advance (T110A, manufactured by TAKARA BIO INC.) and a marketed product of a 35 mm petri dish coated with fibronectin in advance (354457, manufactured by FALCON) were used.

(1) Gene Transfer with a Retrovirus Vector, First Time

Gene transfer using a petri dish coated with Retronectin and that coated with Native fibronectin was carried out according to the same manner as that of Example 21-(2). Gene transfer with polybrene was carried out by the following method. One day before, each 2 mL of human skin fibroblast suspended in 10F-DMEM was seeded on a 35 mm cell culturing petri dish (manufactured by IWAKI CO., LTD.) to $5\times10^4$ cells/mL, and cultured for 1 day. After preparation of a retrovirus vector mixed solution to which polybrene had been added to a final concentration of 4 µg/mL, the supernatant was removed from the petri dish on which the cell has been cultured, this retrovirus vector mixed solution was added, and culturing was initiated in a $CO_2$ incubator at 37° C. (day 0 of culturing). In any method, the virus solutions were mixed at an equal amount in the same combination as that of Example 21-(2), and a group in which the mixed solution was used as it was, and a group in which the virus mixed solution was diluted 10-fold, or 100-fold with 10F-DMEM were set.

(2) Gene Transfer with a Retrovirus Vector, Second Time

According to the same manner as that of Example 30-(1), second time gene transfer was carried out on a culturing 1 day.

(3) Seeding on a Feeder Cell

On the sixth day of culture, according to the same manner as that of Example 5-(4), the gene-introduced cell was seeded on a feeder cell, and culturing was continued.

(4) Culturing

According to the same manner as that of Example 10-(5), culturing was carried out until the 25th day of culture.

(5) Counting of Pluripotent Stem Cells

On the 25th day of culture, the number of a pluripotent stem cell (iPS cell) colony under each condition was counted. The results thereof are shown in Table 40. In addition, the number in the Table indicates an average value of N=2.

TABLE 40

Numbers of iPS cell colonies on the 25th day of culture

| Retrovirus combination condition | Virus concentration | Gene transfer method and iPS cell colony number | | |
|---|---|---|---|---|
| | | Polybrene | Retronectin dish | Fibronectin dish |
| DON5-am-OCT4-IR-SOX2 DON5-am-KLF4 | Stock solution | 2.5 | 10.0 | 8.5 |
| | 10-fold dilution | 8.5 | 18.0 | 0.0 |
| | 100-fold dilution | 1.0 | 11.5 | 0.0 |
| DON5-am-OCT4-IR-SOX2 DON5-am-LIN28-IR-NANOG | Stock solution | 6.0 | 54.0 | 13.5 |

TABLE 40-continued

Numbers of iPS cell colonies on the 25th day of culture

| Retrovirus combination condition | Virus concentration | Gene transfer method and iPS cell colony number | | |
|---|---|---|---|---|
| | | Polybrene | Retronectin dish | Fibronectin dish |
| DON5-am-KLF4 | 10-fold dilution | 38.0 | 67.5 | 0.0 |
| | 100-fold dilution | 2.5 | 47.5 | 0.0 |

As shown in Table 40, a pluripotent stem cell induction efficiency was considerably higher in gene transfer by a standing infecting method using the petri dish coated with Retronectin (in Table, described as Retronectin dish) than in gene transfer with polybrene. A pluripotent stem cell can be stably induced even when the virus solution was used by dilution, in gene transfer by the petri dish coated with Retronectin, while a pluripotent stem cell colony was not formed at all, in gene transfer using the petri dish coated with Native fibronectin (in Table, described as Fibronectin dish). Predominance of Retronectin over Native fibronectin in pluripotent stem cell induction was re-confirmed.

Preparation Example 5

Preparation of Lentivirus Vectors (1) Transfer into pLenti6.3 Plasmid Vector

The pDON-5-KLF4 prepared by Preparation Example 2-(1) was digested with a restriction enzyme NotI, blunted using DNA Blunting Kit (manufactured by TAKARA BIO INC.), and further digested with a restriction enzyme XhoI to obtain a KLF4 fragment. The pDON-5-OCT4-IR-SOX2 prepared in Preparation Example 2-(4) was digested with a restriction enzyme NotI, blunted using DNA Blunting Kit, and further digested with BlnI to obtain an OCT4-IR-SOX2 fragment 1. Similarly, the pDON-5-OCT4-IR-SOX2 was digested with a restriction enzyme BlnI and XhoI to obtain an OCT4-IR-SOX2 fragment 2. In addition, the pDON-5-LIN28-IR-NANOG prepared in Preparation Example 2-(4) was digested with NotI, blunted using DNA Blunting Kit, and further digested with XbaI, thereby, a LIN28-IR-NANOG fragment 1 was obtained. Similarly, pDON-5-LIN28-IR-NANOG was digested with a restriction enzyme XbaI and XhoI, thereby, a LIN28-IR-NANOG fragment 2 was obtained. The pLenti-6.3/V5-TOPO plasmid (manufactured by Invitrogen) was digested with a restriction enzyme EcoRV and XhoI to obtain a pLenti6.3 fragment. The aforementioned respective fragments were subjected to 1.0% agarose electrophoresis, and a DNA fragment having an objective size was extracted and purified. The pLenti6.3 fragment was mixed with the KLF4 fragment, the OCT4-IR-SOX2 fragment 1 and 2, or the LIN28-IR-NANOG fragment 1 and 2, respectively, and ligated using DNA Ligation Kit <Mighty Mix>.
From thus made recombinant plasmids, recombinant plasmids in which each gene was correctly inserted were selected, and named pLenti6.3-KLF4, pLenti6.3-OCT4-IR-SOX2 and pLenti6.3-LIN28-IR-NANOG, respectively.

(2) Production of Lentivirus Vectors

As in Preparation Example 2-(5), the G3T-hi cell was seeded, and cultured for 24 hours. 10 µL of TransIT (registered trademark)-293 (manufactured by TAKARA BIO INC.) was mixed into 500 µL of OPTI-MEM, this was allowed to stand at room temperature for 5 minutes, 4 µg of ViraPower Lentiviral Packaging Mix (manufactured by Invitrogen) and 1 µg of each recombinant plasmid prepared in Preparation Example 5-(1) were added, respectively, to mix, and the mixture was allowed to stand at room temperature for 15 minutes. This mixed solution was added to the G3T-hi cell, culturing was continued and, after 24 hours, the medium was exchanged with 4 mL of 10F-DMEM. After culturing was further continued for 24 hours, the medium containing a virus was recovered, filtered with a 0.45 µm filter to prepare a virus solution containing a lentivirus vector. A name of the lentivirus vector obtained from each recombinant plasmid is shown in Table 41. Three kinds of virus solutions were mixed at an equal amount, and used for infection. A part of the mixed viruses was mixed by adding Lenti-X Concentrator (manufactured by Clonetech) at an amount which is ⅓ of an amount of the virus solution, and this was allowed to stand at 4° C. for 1 hour. Thereafter, after centrifugation at 1,500×g, the supernatant was removed, 10F-DMEM was newly added, and a 20-fold concentrated virus solution was prepared. The virus solution before concentration or after concentration was frozen and stored at −80° C. when it was not used immediately after preparation, and the virus solution was used upon use, by thawing.

TABLE 41

List of lentivirus vectors

| Recombinant plasmid | Lentivirus vector |
|---|---|
| pLenti6.3-OCT4-IR-SOX2 | Lenti-VsvG-OCT4-IR-SOX2 |
| pLenti6.3-LIN28-IR-NANOG | Lenti-VsvG-LIN28-IR-NANOG |
| pLenti6.3-KLF4 | Lenti-VsvG-KLF4 |

Example 31

Induction of a Pluripotent Stem Cell Using a Lentivirus Vector (1) Immobilization of Retronectin on a Culture Plate According to the same manner as that of Example 1-(1), immobilization of Retronectin on a culture plate was carried out, provided that, as a plate to be coated with Retronectin, a non-treatment 12-well plate was used, and each 1 mL of a Retronectin solution (25 µg/mL) was added to each well.

(2) Gene Transfer with a Lentivirus Vector, First Time

Each 500 µL of each mixed virus solution prepared in Preparation Example 5 was added to a 12-well Retronectin immobilization culture plate, or a 12-well culture plate, and each 500 µL of human adult skin fibroblast suspended in 10F-DMEM to $1 \times 10^5$ cells/mL was further added to each well. Regarding polybrene infection condition, polybrene was added to a final concentration of 8 μg/mL. These plates were centrifuged at 32° C. and 1,000×g for 30 minutes, and culturing was initiated in a CO₂ incubator at 37° C. (day 0 of culturing). The set conditions are shown in Table 42.

TABLE 42

Gene transfer conditions

| Condition | Treatment method |
|---|---|
| Condition A | Gene transfer with Retronectin, use of a virus without concentration |
| Condition B | Gene transfer with Retronectin, use of a 20-fold concentrated virus |
| Condition C | Gene transfer with Polybrene, use of a virus without concentration |
| Condition D | Gene transfer with Polybrene, use of a 20-fold concentrated virus |

(3) Gene Transfer with a Lentivirus Vector, Second Time

Gene transfer for the second time was carried out on the first day of culture according to the same manner as that of Example 31-(2). Further, after culturing for 1 day, the supernatant was removed, 1 mL of 10F-DMEM was added, and culturing was continued.

(4) Seeding on a Feeder Cell

On the sixth day of culture, according to the same manner as that of Example 5-(4), the gene-introduced cell was seeded on a feeder cell, and culturing was continued. On the seventh day of culture (after culturing for 1 day from seeding on the feeder cell), the supernatant was removed, 2 mL of a medium for ES cells was added, and culturing was continued until the 32nd day of culture. During this, the medium was exchanged at 2 days interval.

(5) Counting of a Pluripotent Stem Cell Colony

On the 32nd day of culture, the number of a pluripotent stem cell (iPS cell) colony under each condition was counted. The results thereof are shown in Table 43. In addition, regarding the condition A, the results of only one well are shown.

TABLE 43

| Condition | Well 1 | Well 2 |
|---|---|---|
| Condition A | 5 | — |
| Condition B | 3 | 2 |
| Condition C | 0 | 0 |
| Condition D | 0 | 0 |

As shown in Table 43, a pluripotent stem cell colony could be obtained only when infection was carried out using Retronectin, regardless of with or without concentration. That is, it was revealed that, also when a lentivirus vector is used, by performing gene transfer with Retronectin, a pluripotent stem cell can be induced more effectively than gene transfer with polybrene.

INDUSTRIAL APPLICABILITY

According to the present invention, a method for production of a pluripotent stem cell at a higher frequency as compared with the conventional production method is provided. Since a pluripotent stem cell contained in a cell population obtained by the present invention can be differentiated into a desired cell by the known means, it is very useful in preparation of a cell for transplant into a living recipient, or in use for basic research.

SEQUENCE LISTING FREE TEXT

SEQ ID NO:1; Primer hSOX2-F to amplify the SOX2 gene.
SEQ ID NO:2; Primer hSOX2-R to amplify the SOX2 gene.
SEQ ID NO:3; Primer hKLF4-F to amplify the KLF4 gene.
SEQ ID NO:4; Primer hKLF4-R to amplify the KLF4 gene.
SEQ ID NO:5; Primer IRES-F-SalI to amplify the IRES sequence.
SEQ ID NO:6; Primer IRES-R-NotI to amplify the IRES sequence.
SEQ ID NO:7; Primer OCT4EndoqP-F1 to amplify the endogenous OCT4 gene.
SEQ ID NO:8; Primer OCT4EndoP-R1 to amplify the endogenous OCT4 gene.
SEQ ID NO:9; Primer SOX2EndoP-F2 to amplify the endogenous SOX2 gene.
SEQ ID NO:10; Primer SOX2EndoP-R2 to amplify the endogenous SOX2 gene.

The invention claimed is:

1. A method for production of a cell population containing a pluripotent stem cell, said method comprising a step of infecting a somatic cell with a retrovirus vector(s) carrying genes encoding nuclear reprogramming factors in the presence of a sole functional substance having an activity of binding to a retrovirus and an activity of improving pluripotent stem cell induction efficiency, wherein the functional substance consists of a fibronectin fragment of full-length fibronectin having a heparin-II binding region.

2. The method according to claim 1, wherein the somatic cell is infected with a retrovirus vector(s) carrying genes encoding the nuclear reprogramming factors selected from the group consisting of OCT4, SOX2, c-MYC, KLF4, NANOG and LIN28.

3. A method for production of a pluripotent stem cell, said method comprising a step of producing a cell population containing a pluripotent stem cell by the method as defined in claim 1, and a step of isolating a pluripotent stem cell from the resulting cell population.

* * * * *